United States Patent
Edgerton et al.

(10) Patent No.: US 9,907,958 B2
(45) Date of Patent: *Mar. 6, 2018

(54) HIGH DENSITY EPIDURAL STIMULATION FOR FACILITATION OF LOCOMOTION, POSTURE, VOLUNTARY MOVEMENT, AND RECOVERY OF AUTONOMIC, SEXUAL, VASOMOTOR, AND COGNITIVE FUNCTION AFTER NEUROLOGICAL INJURY

(71) Applicants: THE REGENTS OF THE UNIVERSITY OF CALIFORNIA, Oakland, CA (US); UNIVERSITY OF LOUISVILLE RESEARCH FOUNDATION, INC., Louisville, KY (US); CALIFORNIA INSTITUTE OF TECHNOLOGY, Pasadena, CA (US)

(72) Inventors: Victor Reggie Edgerton, Los Angeles, CA (US); Roland R. Roy, Playa Vista, CA (US); Yury Gerasimenko, Los Angeles, CA (US); Joel W. Burdick, Pasadena, CA (US); Susan J. Harkema, Louisville, KY (US); Jonathan Hodes, Louisville, KY (US); Yu-Chong Tai, Pasadena, CA (US); Mandheerej S. Nandra, Pasadena, CA (US); Claudia A. Angeli, Louisville, KY (US); Thomas Anthony Desautels, Pasadena, CA (US)

(73) Assignees: The Regents of the University of California, Oakland, CA (US); California Institute of Technology, Pasadena, CA (US); University of Louisville Research Foundation, Inc., Louisville, KY (US)

(*) Notice: Subject to any disclaimer, the term of this patent is extended or adjusted under 35 U.S.C. 154(b) by 66 days.

This patent is subject to a terminal disclaimer.

(21) Appl. No.: 14/790,729

(22) Filed: Jul. 2, 2015

(65) Prior Publication Data

US 2016/0030748 A1 Feb. 4, 2016

Related U.S. Application Data

(63) Continuation of application No. 13/978,035, filed as application No. PCT/US2012/020112 on Jan. 3, 2012, now Pat. No. 9,101,769.

(Continued)

(51) Int. Cl.
*A61N 1/18* (2006.01)
*A61N 1/36* (2006.01)
(Continued)

(52) U.S. Cl.
CPC ....... *A61N 1/36103* (2013.01); *A61H 1/0237* (2013.01); *A61H 1/0274* (2013.01);
(Continued)

(58) Field of Classification Search
CPC .............. A61N 1/36103; A61N 1/0237; A61N 1/0274; A61N 1/0551; A61N 1/0553;
(Continued)

(56) References Cited

U.S. PATENT DOCUMENTS 3,543,761 A 12/1970 Bradley
3,662,758 A 5/1972 Glover
(Continued)

FOREIGN PATENT DOCUMENTS

JP 2002-200178 7/2002
JP 2008-067917 A 3/2008
(Continued)

OTHER PUBLICATIONS

U.S. Appl. No. 14/925,791, filed Oct. 28, 2015.
(Continued)

*Primary Examiner* — Michael Carey
(74) *Attorney, Agent, or Firm* — K&L Gates LLP; Louis C. Cullman; Brian J. Novak

(57) ABSTRACT

Methods of enabling locomotor control, postural control, voluntary control of body movements (e.g., in non-weight bearing conditions), and/or autonomic functions in a human subject having spinal cord injury, brain injury, or neurological neuromotor disease are described.

20 Claims, 25 Drawing Sheets

Related U.S. Application Data

(60) Provisional application No. 61/429,368, filed on Jan. 3, 2011, provisional application No. 61/437,418, filed on Jan. 28, 2011, provisional application No. 61/469,555, filed on Mar. 30, 2011.

(51) Int. Cl.
| | | |
|---|---|---|
| *A61N 1/05* | (2006.01) | |
| *A63B 21/00* | (2006.01) | |
| *A61H 1/02* | (2006.01) | |
| *A63B 69/00* | (2006.01) | |
| *A63B 22/02* | (2006.01) | |

(52) U.S. Cl.
CPC ......... *A61N 1/0551* (2013.01); *A61N 1/0553* (2013.01); *A61N 1/0556* (2013.01); *A61N 1/36003* (2013.01); *A61N 1/36153* (2013.01); *A63B 21/00181* (2013.01); *A63B 22/0235* (2013.01); *A63B 69/0064* (2013.01); *A63B 2213/004* (2013.01); *A63B 2220/805* (2013.01); *A63B 2230/60* (2013.01); *F04C 2270/0421* (2013.01)

(58) Field of Classification Search
CPC ............... A61N 1/0556; A61N 1/36003; A61N 1/36153; A63B 21/00181; A63B 22/0235; A63B 69/0064; A63B 2213/004; A63B 2220/805; A63B 2230/60; F04C 2270/0421
USPC ........................................ 607/48, 49, 70, 117
See application file for complete search history.

(56) References Cited

U.S. PATENT DOCUMENTS

| | | | |
|---|---|---|---|
| 3,724,467 | A | 4/1973 | Avery et al. |
| 4,044,774 | A | 8/1977 | Corbin et al. |
| 4,102,344 | A | 6/1978 | Conway et al. |
| 4,141,365 | A | 2/1979 | Fischell et al. |
| 4,285,347 | A | 8/1981 | Hess |
| 4,340,063 | A | 7/1982 | Maurer |
| 4,379,462 | A | 4/1983 | Borkan et al. |
| 4,414,986 | A | 11/1983 | Dickhudt et al. |
| 4,538,624 | A | 9/1985 | Tarjan |
| 4,549,556 | A | 10/1985 | Tajan et al. |
| 4,800,898 | A | 1/1989 | Hess et al. |
| 4,934,368 | A | 6/1990 | Lynch |
| 5,002,053 | A * | 3/1991 | Garcia-Rill ........ A61N 1/36003 607/49 |
| 5,031,618 | A | 7/1991 | Mullett |
| 5,081,989 | A | 1/1992 | Graupe |
| 5,121,754 | A | 6/1992 | Mullett |
| 5,344,439 | A | 9/1994 | Otten |
| 5,354,320 | A | 10/1994 | Schaldach |
| 5,374,285 | A | 12/1994 | Vaiani et al. |
| 5,417,719 | A | 5/1995 | Hull et al. |
| 5,562,718 | A | 10/1996 | Palermo |
| 5,643,330 | A | 7/1997 | Holsheimer et al. |
| 5,733,322 | A | 3/1998 | Starkebaum |
| 5,983,141 | A | 11/1999 | Sluijter et al. |
| 6,066,163 | A | 5/2000 | John |
| 6,104,957 | A | 8/2000 | Alo et al. |
| 6,122,548 | A | 9/2000 | Starkebaum et al. |
| 6,308,103 | B1 | 10/2001 | Gielen |
| 6,319,241 | B1 | 11/2001 | King et al. |
| 6,470,213 | B1 | 10/2002 | Alley |
| 6,587,724 | B2 | 7/2003 | Mann |
| 6,662,053 | B2 | 12/2003 | Borkan |
| 6,666,831 | B1 | 12/2003 | Edgerton et al. |
| 6,685,729 | B2 | 2/2004 | Gonzalez |
| 6,819,956 | B2 | 11/2004 | DiLorenzo |
| 6,839,594 | B2 | 1/2005 | Cohen |
| 6,871,099 | B1 | 3/2005 | Whitehurst et al. |
| 6,892,098 | B2 | 5/2005 | Ayal |
| 6,895,280 | B2 | 5/2005 | Meadows |
| 6,895,283 | B2 | 5/2005 | Erickson et al. |
| 6,937,891 | B2 | 8/2005 | Leinders |
| 6,950,706 | B2 | 9/2005 | Rodriguez |
| 6,975,907 | B2 | 12/2005 | Zanakis |
| 6,988,006 | B2 | 1/2006 | King et al. |
| 6,999,820 | B2 | 2/2006 | Jordan |
| 7,020,521 | B1 | 3/2006 | Brewer et al. |
| 7,024,247 | B2 | 4/2006 | Gliner et al. |
| 7,035,690 | B2 | 4/2006 | Goetz |
| 7,047,084 | B2 | 5/2006 | Erickson et al. |
| 7,065,408 | B2 * | 6/2006 | Herman ............... A61N 1/3604 482/54 |
| 7,096,070 | B1 | 8/2006 | Jenkins et al. |
| 7,110,820 | B2 | 9/2006 | Tcheng |
| 7,127,287 | B2 | 10/2006 | Duncan |
| 7,127,296 | B2 | 10/2006 | Bradley |
| 7,127,297 | B2 | 10/2006 | Law et al. |
| 7,184,837 | B2 | 2/2007 | Goetz |
| 7,200,443 | B2 | 4/2007 | Faul |
| 7,209,787 | B2 | 4/2007 | DiLorenzo |
| 7,228,179 | B2 | 6/2007 | Campen |
| 7,239,920 | B1 | 7/2007 | Thacker et al. |
| 7,251,529 | B2 | 7/2007 | Greenwood-Van |
| 7,252,090 | B2 | 8/2007 | Goetz |
| 7,313,440 | B2 | 12/2007 | Miesel et al. |
| 7,330,760 | B2 | 2/2008 | Heruth et al. |
| 7,337,005 | B2 | 2/2008 | Kim |
| 7,377,006 | B2 | 2/2008 | Kim |
| 7,340,298 | B1 | 3/2008 | Barbut |
| 7,415,309 | B2 | 8/2008 | McIntyre |
| 7,463,927 | B1 | 12/2008 | Chaouat |
| 7,463,928 | B2 | 12/2008 | Lee |
| 7,467,016 | B2 | 12/2008 | Colborn |
| 7,493,170 | B1 | 2/2009 | Segel et al. |
| 7,496,404 | B2 | 2/2009 | Meadows et al. |
| 7,502,652 | B2 | 3/2009 | Gaunt |
| 7,584,000 | B2 | 9/2009 | Erickson |
| 7,590,454 | B2 | 9/2009 | Garabedian et al. |
| 7,603,178 | B2 | 10/2009 | North et al. |
| 7,628,750 | B2 | 12/2009 | Cohen |
| 7,660,636 | B2 | 2/2010 | Castel et al. |
| 7,697,995 | B2 | 4/2010 | Cross et al. |
| 7,729,781 | B2 | 6/2010 | Swoyer et al. |
| 7,734,340 | B2 | 6/2010 | De Ridder |
| 7,734,351 | B2 | 6/2010 | Testerman |
| 7,769,463 | B2 | 8/2010 | Katsnelson |
| 7,797,057 | B2 | 9/2010 | Harris |
| 7,801,601 | B2 | 9/2010 | Maschino et al. |
| 7,813,803 | B2 | 10/2010 | Heruth et al. |
| 7,890,182 | B2 | 2/2011 | Parramon et al. |
| 7,949,395 | B2 | 5/2011 | Kuzma |
| 7,949,403 | B2 | 5/2011 | Palermo |
| 7,987,000 | B2 | 7/2011 | Moffitt et al. |
| 7,991,465 | B2 | 8/2011 | Bartic et al. |
| 8,019,427 | B2 | 9/2011 | Moffitt |
| 8,050,773 | B2 | 11/2011 | Zhu |
| 8,108,052 | B2 | 1/2012 | Boling |
| 8,131,358 | B2 | 3/2012 | Moffitt |
| 8,155,750 | B2 | 4/2012 | Jaax |
| 8,170,660 | B2 | 5/2012 | Dacey |
| 8,190,262 | B2 | 5/2012 | Gerber |
| 8,195,304 | B2 | 6/2012 | Strother et al. |
| 8,239,038 | B2 | 8/2012 | Wolf |
| 8,260,436 | B2 | 9/2012 | Gerber et al. |
| 8,311,644 | B2 | 11/2012 | Moffitt |
| 8,332,029 | B2 | 12/2012 | Glukhovsky et al. |
| 8,346,366 | B2 | 1/2013 | Arle |
| 8,352,036 | B2 | 1/2013 | Dimarco |
| 8,355,791 | B2 | 1/2013 | Moffitt |
| 8,355,797 | B2 | 1/2013 | Caparso et al. |
| 8,364,273 | B2 | 1/2013 | De Ridder |
| 8,369,961 | B2 | 2/2013 | Christman |
| 8,412,345 | B2 | 4/2013 | Moffitt |
| 8,428,728 | B2 | 4/2013 | Sachs |
| 8,442,655 | B2 | 5/2013 | Moffitt et al. |
| 8,452,406 | B2 | 5/2013 | Arcot-Krishmamur |
| 8,805,542 | B2 | 8/2014 | Tai |

(56) References Cited

U.S. PATENT DOCUMENTS

| | | |
|---|---|---|
| 9,101,769 B2 * | 8/2015 | Edgerton ............ A61N 1/0551 |
| 2002/0055779 A1 | 5/2002 | Andrews |
| 2002/0111661 A1 | 8/2002 | Cross et al. |
| 2003/0032992 A1 | 2/2003 | Thacker |
| 2003/0078633 A1 | 4/2003 | Firlik et al. |
| 2004/0044380 A1 | 3/2004 | Buringa |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Blazer et al. |
| 2005/0004622 A1 | 1/2005 | Cullen et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Barrera et al. |
| 2005/0246004 A1 | 11/2005 | Cameron et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2007/0016097 A1 | 1/2007 | Farquhar et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0083240 A1 | 4/2007 | Peterson et al. |
| 2007/0156179 A1 | 7/2007 | S.E. |
| 2007/0179534 A1 | 8/2007 | Firlik et al. |
| 2007/0191709 A1 | 8/2007 | Swanson |
| 2007/0233204 A1 | 10/2007 | Lima et al. |
| 2007/0265691 A1 | 11/2007 | Swanson |
| 2008/0009927 A1 | 1/2008 | Vilimis |
| 2008/0046049 A1 | 2/2008 | Skubitz et al. |
| 2008/0051851 A1 | 2/2008 | Lin |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0221653 A1 | 9/2008 | Agrawal |
| 2008/0228250 A1 | 9/2008 | Mironer |
| 2008/0234791 A1 | 9/2008 | Arle et al. |
| 2008/0294226 A1 * | 11/2008 | Moffitt .................. A61N 1/0553 607/74 |
| 2009/0112281 A1 | 4/2009 | Miyazawa et al. |
| 2009/0204173 A1 | 8/2009 | Fang et al. |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0185253 A1 | 7/2010 | Dimarco et al. |
| 2010/0217355 A1 | 8/2010 | Tass et al. |
| 2010/0241191 A1 | 9/2010 | Testerman |
| 2010/0274312 A1 | 10/2010 | Alataris |
| 2010/0312304 A1 | 12/2010 | York et al. |
| 2011/0034977 A1 | 2/2011 | Janik et al. |
| 2011/0054567 A1 | 3/2011 | Lane |
| 2011/0054568 A1 | 3/2011 | Lane |
| 2011/0077660 A1 | 3/2011 | Janik et al. |
| 2011/0130804 A1 | 6/2011 | Lin et al. |
| 2011/0160810 A1 | 6/2011 | Griffith |
| 2011/0184489 A1 | 7/2011 | Nicolelis et al. |
| 2011/0218590 A1 | 9/2011 | Degiorgio et al. |
| 2011/0218594 A1 | 9/2011 | Doron |
| 2011/0224665 A1 | 9/2011 | Crosby et al. |
| 2011/0224753 A1 | 9/2011 | Palermo |
| 2011/0224757 A1 | 9/2011 | Zdeblick et al. |
| 2011/0237921 A1 | 9/2011 | Askin et al. |
| 2012/0035684 A1 | 2/2012 | Thompson et al. |
| 2012/0059432 A1 | 3/2012 | Emborg et al. |
| 2012/0071950 A1 | 3/2012 | Archer |
| 2012/0109251 A1 | 5/2012 | Lebedev |
| 2012/0123293 A1 | 5/2012 | Shah et al. |
| 2012/0136408 A1 | 5/2012 | Grill et al. |
| 2012/0165899 A1 | 6/2012 | Gliner |
| 2012/0172946 A1 | 7/2012 | Altaris et al. |
| 2012/0179222 A1 | 7/2012 | Jaax |
| 2012/0232615 A1 | 9/2012 | Barolat |
| 2012/0277834 A1 | 11/2012 | Mercanzini et al. |
| 2012/0330391 A1 | 12/2012 | Bradley et al. |
| 2013/0030501 A1 | 1/2013 | Feler et al. |
| 2013/0035745 A1 | 2/2013 | Ahmed et al. |
| 2013/0085361 A1 | 4/2013 | Mercanzini et al. |
| 2013/0096640 A1 | 4/2013 | Possover |
| 2013/0123568 A1 | 5/2013 | Hamilton et al. |
| 2013/0253299 A1 | 9/2013 | Weber |
| 2013/0253611 A1 | 9/2013 | Lee |
| 2014/0163640 A1 | 6/2014 | Edgerton et al. |
| 2014/0180361 A1 * | 6/2014 | Burdick ............... A61N 1/0553 607/49 |
| 2014/0316484 A1 | 10/2014 | Edgerton |
| 2014/0316503 A1 | 10/2014 | Tai |
| 2015/0217120 A1 | 8/2015 | Nandra et al. |
| 2015/0231396 A1 | 8/2015 | Burdick et al. |
| 2016/0175586 A1 | 6/2016 | Edgerton et al. |
| 2016/0220813 A1 | 8/2016 | Edegerton et al. |
| 2016/0310739 A1 | 10/2016 | Burdick et al. |
| 2017/0157389 A1 | 6/2017 | Tai et al. |

FOREIGN PATENT DOCUMENTS

| | | |
|---|---|---|
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | 1997/047357 A1 | 12/1997 |
| WO | 2003/026735 A2 | 4/2003 |
| WO | 2003/092795 A1 | 11/2003 |
| WO | 2004/087116 A2 | 10/2004 |
| WO | 2005/051306 A2 | 6/2005 |
| WO | 2005/087307 A2 | 9/2005 |
| WO | 2007/081764 A2 | 7/2007 |
| WO | 2007/107831 A2 | 9/2007 |
| WO | 2008/070807 A3 | 6/2008 |
| WO | 2008/109862 A2 | 9/2008 |
| WO | 2008/121891 A1 | 10/2008 |
| WO | 2009/042217 A1 | 4/2009 |
| WO | 2009/111142 A2 | 9/2009 |
| WO | 2010/114998 A1 | 10/2010 |
| WO | 2010/124128 A1 | 10/2010 |
| WO | 2011/005607 A1 | 1/2011 |
| WO | 2012/094346 A2 | 7/2012 |
| WO | 2012/100260 A2 | 7/2012 |
| WO | 2012/129574 A2 | 9/2012 |
| WO | 2013/071307 A1 | 5/2013 |

(56) References Cited

FOREIGN PATENT DOCUMENTS

| WO | 2013/071309 A1 | 5/2013 |
|---|---|---|
| WO | 2014/144785 A1 | 9/2014 |
| WO | 2015/106286 A1 | 7/2015 |

OTHER PUBLICATIONS

U.S. Appl. No. 15/096,014, filed Apr. 11, 2016.
Ganley et al., Epidural spinal cord stimulation improves locomoter performance in low ASIA C, Wheel-chair-Dependent, spinal cord-injured individuals: Insights from metabolic response. Top. Spinal Cord Inj. Rehabil; 11(2); 60-63 (2005).
"Hermann et al., Spinal cord stimulation facilitates functional walking in a chronic, incomplete spinal cord injured. Spinal Cord, vol. 40, pp. 65-68 (2002).".
International Search Report for International Application Serial No. PCT/US2012/020112 filed on Jan. 3, 2012.
International Search Report for International Application Serial No. PCT/US2012/022257 filed on Jan. 23, 2012.
International Search Report for International Application Serial No. PCT/US2012/030624 filed on Mar. 26, 2012.
International Search Report for International Application Serial No. PCT/US2014/029340 filed on Mar. 14, 2014.
Nandra et al., A parylene-based microelectrode arrary implant for spinal cord stimulation in rats. Conf. Proc. IEEE Eng. Med. Biol. Soc., pp. 1007-1010 (2011).
Nandra et al., A wireless microelectode implant for spinal cord stimulation and recording in rats. Presentation Abstract, 2013.
Transcutaneous Lumbar Spinal Cord Stimulation, http://www.restrorativeneurology.org (available online and attached), International Society for Restorative Neurology, 2012.
Rodger et al., High density flexible parylene-based multielectrode arrays for retinal and spinal cord stimulation. Proc. of the 14th International Conference on Solid-State Sensors, Actuators and Microsystems, pp. 1385-1888 (2007).
International Search Report for International Application Serial No. PCT/US2012/064874 filed on Nov. 13, 2012.
International Search Report for International Application Serial No. PCT/US2012/064878 filed on Nov. 13, 2012.
Dimitrijevic et al., Clinical elements for the neuromuscular stimulation and functional electrical stimulation protocols in the practice of neurorehabilitation, Artificial Organs, 26(3): 256-259 (2002).
Dimitrijevic et al., Evidence for a spinal central pattern generator in humans. Annals New York Academy Sciences, 860: 360-376 (1998).
Gerasimenko et al., Control of locomotor activity in humans and animals in the absence of supraspinal influences. Neuroscience and Behavioral Physiology, 32(4): 417-423 (2002).
Hofstoetter et al., Modification of reflex responses to lumbar posterior root stimulation by motor tasks in healthy subjects. Artificial Organs, 32(8):644-648 (2008).
Hofstoetter et al., Model of spinal cord reflex circuits in humans: stimulation frequency-dependence of segmental activities and their interactions. Second Congress International Society of Intraoperative Neurophysiology (ISIN), Dubrovnik, Croatia, pp. 8-10 (2009).
International Search Report and Written Opinion dated May 19, 2015 for International Application Serial No. PCT/US2015/011263 filed on Jan. 13, 2015.
Jilge et al, Initiating extension of the lower limbs in subjects with complete spinal cord injury by epidural lumbar cord stimulation. Exp Brain Res., 154: 308-326 (2004).
Ladenbauer et al., Stimulation of the human lumbar spinal cord with implanted and surface electrodes: a computer simulation study. IEEE Transactions on Neural Systems and Rehabilitation Engineering, 18(6):637-645 (2010).
Minassian et al., Transcutaneous stimulation of the human lumbar spinal cord: Facilitating locomotor output in spinal cord injury. Society for Neuroscience, Conference Proceedings, Neuroscience 2010, San Diego, CA, Abstract Viewer/ Itinerary Planner No. 286. 19, Abstract & Poster attached (2010).
Minassian et al., Human lumbar cord circuitries can be activated by extrinsic tonic input to generate locomotor-like activity. Human Movement Science, 26(2):275-295 (2007).
Minassian et al., Posterior root-muscle reflexes elicited by transcutaneous stimulation of the human lumbosacral cord. Muscle & Nerve, 35(3):327-336 (2007) Article first published online in 2006.
Minassian et al., Stepping-like movements in humans with complete spinal cord injury induced by epidural stimulation of the lumbar cord: electromyographic study of compound muscle action potentials. Spinal Cord, 42: 401-416 (2004).
Minassian et al., Peripheral and central afferent input to the lumbar cord. Biocybernetics and Biomedical Engineering, 25(3): 11-29 (2005).
Minassian et al., Human lumbar cord model of the locomotor central pattern generator. Second Congress International Society of Intraoperative Neurophysiology (ISIN), Dubrovnik, Croatia, pp. 11-13 (2009).
Minassian et al., Posterior root-muscle reflex, Second Congress International Society of Intraoperative Neurophysiology (ISIN), Dubrovnik, Croatia, pp. 77-80 (2009).
Murg et al., Epidural electric stimulation of posterior structures of the human lumbar spinal cord: 1. Muscle twitches—a functional method to define the site of stimulation. Spinal Cord, 38: 394-402 (2000).
Rattay et al., Epidural electrical stimulation of posterior structures of the human lumbosacral cord: 2. Quantitative analysis by computer modeling. Spinal Cord, 38: 473-489 (2000).
Supplementary European Search Report and Opinion for European Patent Application Serial No. 12848368.2 filed on Nov. 13, 2012.
Ward, Electrical Stimulation Using Kilohertz-Frequency Alternating Current. Physical therapy, 89:181-190 (2009) (published online Dec. 18, 2008).
Danner et al., Body position influences which neural structures are recruited by lumbar transcutaneous spinal cord stimulation. PLoS ONE 11(1):e0147479 (2016).
Dimitrijevic et al., Electrophysiological characteristics of H-reflexes elicited by percutaneous stimulation of the cauda equina. Abstract No. 4927, 34th Annual Meeting of the Society for Neuroscience, San Diego, CA (2004).
Hofstoetter et al., Modification of spasticity by transcutaneous spinal cord stimulation in individuals with incomplete spinal cord injury. The Journal of Spinal Cord Medicine, 37:2, 202-211 (2014).
Hofstoetter et al., Effects of transcutaneous spinal cord stimulation on voluntary locomotor activity in an incomplete spinal cord injured individual. Biomed Tech, 58 (Suppl. 1) 2013.
Krenn et al., Selectivity of transcutaneous stimulation of lumbar posterior roots at different spinal levels in humans. Biomed Tech, 58 (Suppl. 1) (2013).
Minassian et al., Neurophysiology of the human lumbar locomotor pattern generator. 2010. 15th Annual Conference of the International Functional Electrical Stimulation Society. Annual IFESS Conference Proceedings.
Minassian et al., Mechanisms of rhythm generation of the human lumbar spinal cord in repose to tonic stimulation without and with step-related sensory feedback. Biomed Tech, 58 (Suppl. 1) (2013).
Minassian et al., Neuromodulation of lower limb motor control in restorative neurology. Clinical Neurology and Neurosurgery, 114:489-497 (2012).
Rasmussen, Carl Edward. Gaussian Processes in Machine Learning. Machine Learning, L.N.A.I. 3176, p. 63-71 (2003).
Gerasimenko et al., Noninvasive reactivation of motor descending control after paralysis. Journal of Neurotrauma, 2015 (article has been peer-reviewed and accpeted for publication, 49 pages).
Office Action for European Patent Application No. 12760696.0 dated Nov. 9, 2017.
Office Action for Canadian Patent Application No. 2,823,592 dated Oct. 5, 2017.
Office Action for Australian Patent Application No. 2017203132 dated Oct. 13, 2017.

\* cited by examiner

*FIG. 3*
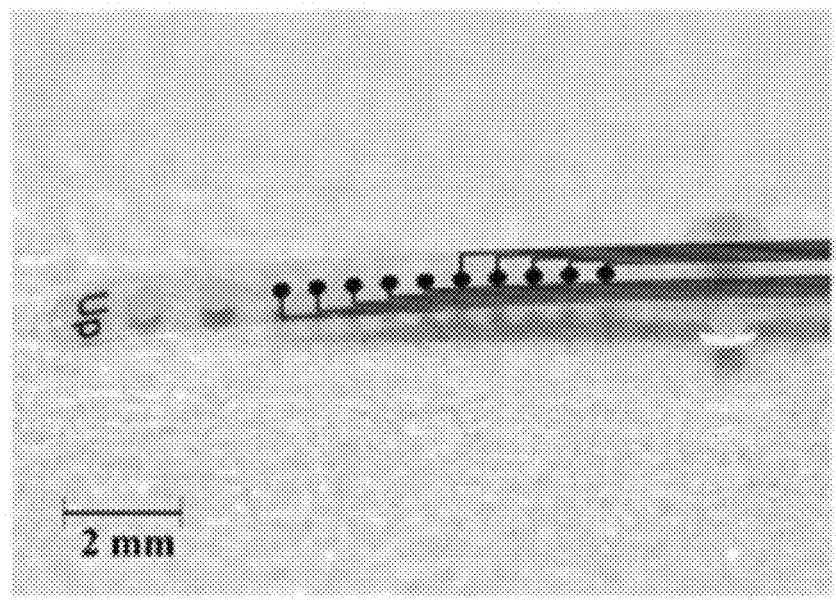
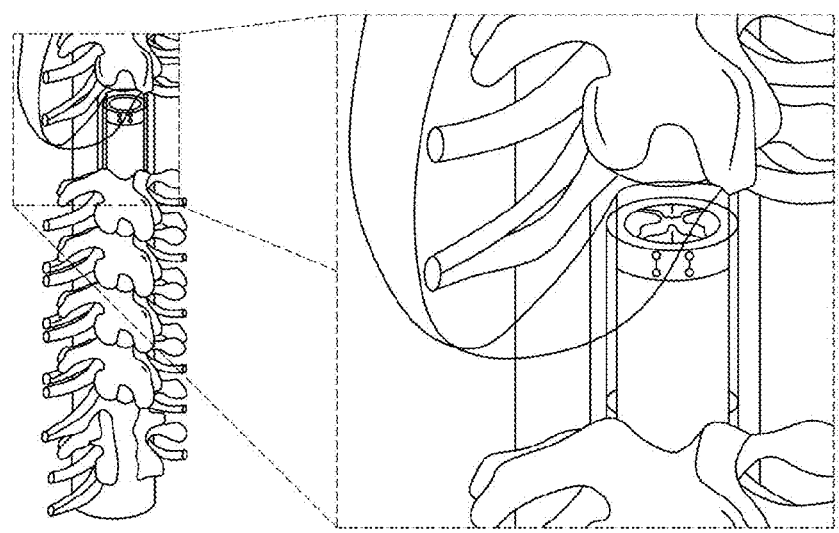
*FIG. 4*

| AIS Evaluation |||| 
|---|---|---|---|
| Neuro Level | T2 | Grade | B |
| Motor Score || Sensory Score ||
| Right Upper Extremity | Left Upper Extremity | Right Light Touch | Left Light Touch |
| 25 | 25 | 50 | 50 |
| Right Lower Extremity | Left Lower Extremity | Right Pin Prick | Left Pin Prick |
| 0 | 0 | 38 | 33 |

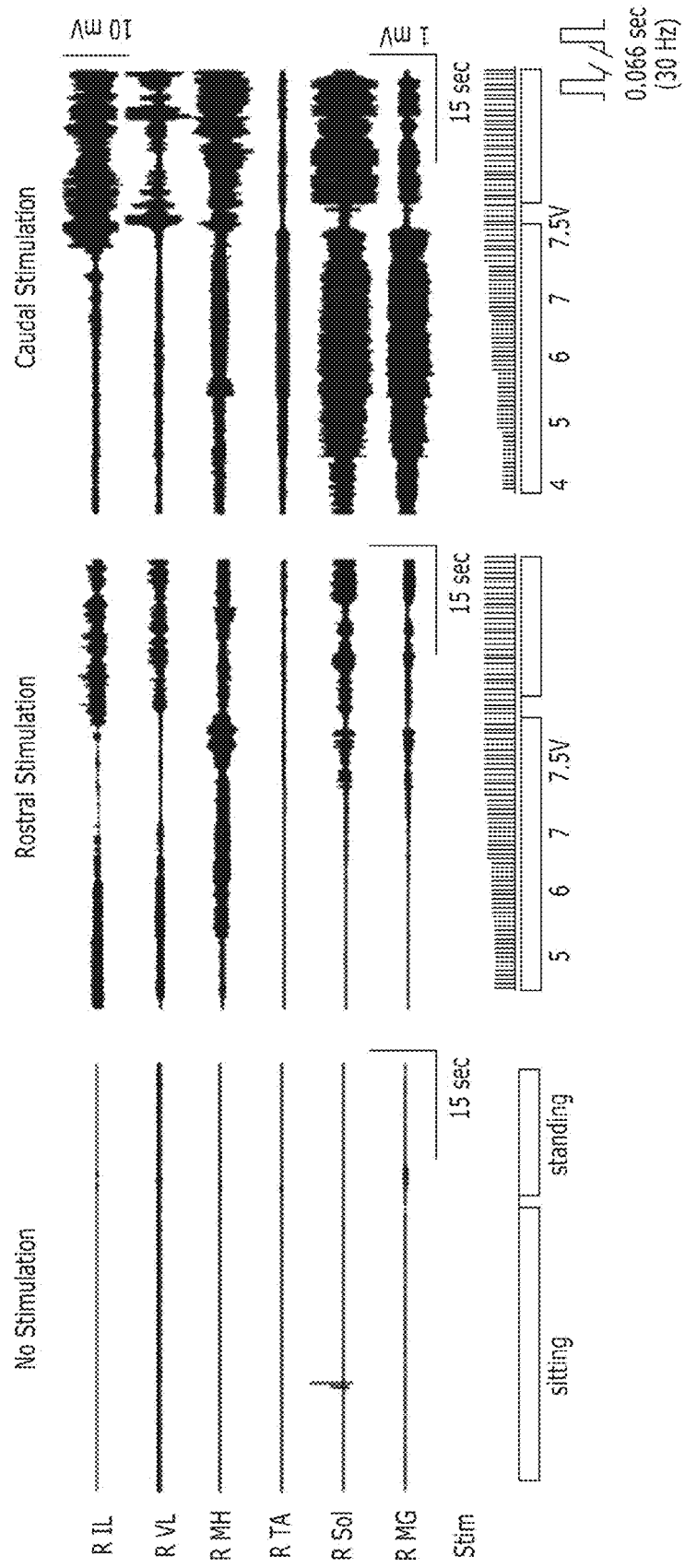

FIG. 17D
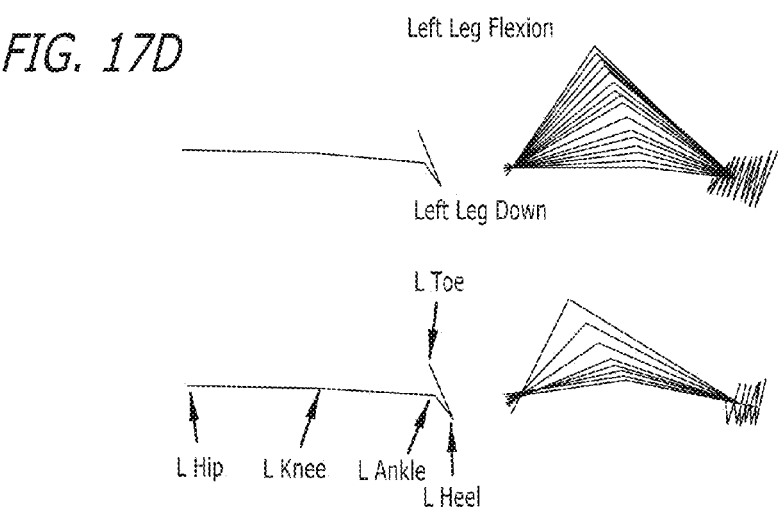
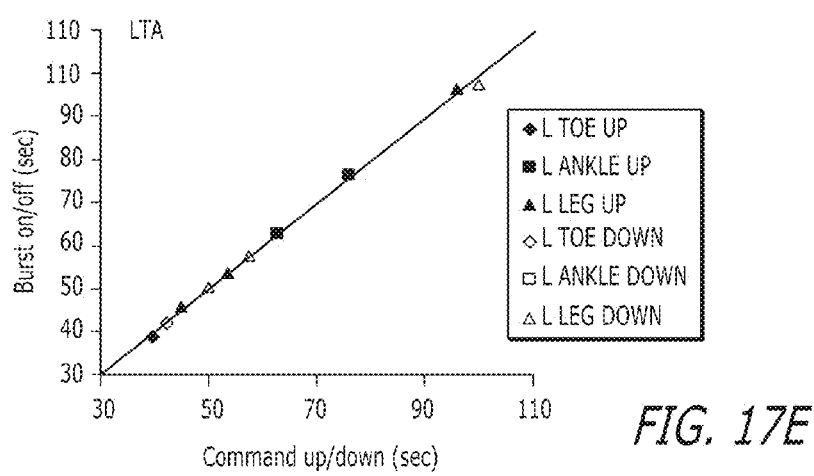
FIG. 17E

HIGH DENSITY EPIDURAL STIMULATION FOR FACILITATION OF LOCOMOTION, POSTURE, VOLUNTARY MOVEMENT, AND RECOVERY OF AUTONOMIC, SEXUAL, VASOMOTOR, AND COGNITIVE FUNCTION AFTER NEUROLOGICAL INJURY

CROSS REFERENCE TO RELATED APPLICATION(S)

This application is a continuation of U.S. patent application Ser. No. 13/978,035, filed Feb. 17, 2014, now U.S. Pat. No. 9,101,769, which is a national phase entry of PCT/US2012/020112, filed Jan. 3, 2012, which claims the benefit of U.S. Provisional Application No. 61/429,368, filed Jan. 3, 2011; U.S. Provisional Application No. 61/437,418, filed Jan. 28, 2011; and U.S. Provisional Application No. 61/469,555, filed Mar. 30, 2011, each of which is incorporated herein by reference in its entirety.

STATEMENT REGARDING FEDERALLY SPONSORED RESEARCH OR DEVELOPMENT

This invention was made with Government support under Grant No. W81XWH-09-2-0024, awarded by the United States Army, Medical Research and Materiel Command; and Grant No. EB007615, awarded by the National Institutes of Health. The Government has certain rights in this invention.

BACKGROUND OF THE INVENTION

Field of the Invention

The present invention relates to the field neurological rehabilitation including traumatic spinal cord injury, non-traumatic spinal cord injury, stroke, movement disorders, brain injury, and other diseases or injuries that result in paralysis and/or nervous system disorder. Devices, pharmacological agents, and methods are provided to facilitate recovery of posture, locomotion, and voluntary movements of the arms, trunk, and legs, and recovery of autonomic, sexual, vasomotor, and cognitive function, in a human subject having spinal cord injury, brain injury, or any other neurological disorder.

Description of the Related Art

Serious spinal cord injuries (SCI) affect approximately 250,000 people in the United States, and roughly 11,000 new injuries occur each year. Of these injuries, approximately 50% are complete spinal cord injuries in which there is essentially total loss of sensory motor function below the level of the spinal lesion.

For chronic SCI humans, impressive levels of standing and stepping recovery has been demonstrated in certain incomplete SCI subjects with task specific physical rehabilitation training. A recent clinical trial demonstrated that 92% of the subjects regained stepping ability to almost a functional speed of walking three months after a severe yet incomplete injury (Dobkin et al., *Neurology*, 66(4): 484-93 (2006)) and in chronic subjects months to years after injury (Harkema et. al., *Archives of Physical Medicine and Rehabilitation:* 2011 epub). Furthermore, improved coordination of motor pool activation can be achieved with training in patients with incomplete SCI (Field-Fote et al., *Phys. Ther.*, 82 (7): 707-715 (2002)). On the other hand, there is no generally accepted evidence that an individual with a clinically complete SCI can be trained to the point where they could stand or locomote even with the aid of a "walker" (Wernig, *Arch Phys Med Rehabil.*, 86(12): 2385-238 (2005)) and no one has shown the ability to regain voluntary movements and/or to recover autonomic, sexual, vasomotor, and/or improved cognitive function after a motor complete spinal cord injury.

To date, the consistently most successful intervention for regaining weight-bearing stepping in humans is weight-bearing step training, but that has been the case primarily in subjects with incomplete injuries.

The most effective future strategies for improving motor and autonomic functions that improve the quality of life post-SCI will likely involve the combination of many different technologies and strategies, as neurological deficits such as spinal cord injuries are complex, and there is a wide variability in the deficit profile among patients. In the long run, neuro-regenerative strategies hold significant promise for functional sensory-motor recovery from traumatic and progressive neurological deficits. Progress is already being made particularly in the case of acute treatment of incomplete spinal injuries. However, even when these strategies are perfected, other remedies will be needed. It is naive to think that neuro-regenerative approaches will recover fully functional postural and locomotor function as well as voluntary control of lower limb, and voluntary upper limb movement following a motor complete spinal injury.

SUMMARY OF THE INVENTION

Embodiments of the invention are for use with a human patient (or subject) who has a spinal cord with at least one selected spinal circuit and a neurologically derived paralysis in a portion of the patient's body. By way of non-limiting examples, when activated, the selected spinal circuit may (a) enable voluntary movement of muscles involved in at least one of standing, stepping, reaching, grasping, voluntarily changing positions of one or both legs, voiding the patient's bladder, voiding the patient's bowel, postural activity, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, ischemia, stroke, amyotrophic lateral sclerosis (ALS), primary lateral sclerosis (PLS), and cerebral palsy.

One exemplary embodiment is a method that includes positioning the human patient in a training device. The training device is configured to assist with physical training (e.g., at least one of standing, stepping, reaching, moving one or both legs, moving one or both feet, grasping, and stabilizing sitting posture) that is configured to induce neurological signals (e.g., at least one of postural proprioceptive signals, locomotor proprioceptive signals, and supraspinal signals) in the portion of the patient's body having the paralysis. The training device may include a robot training device configured to move automatically at least a portion of the portion of the patient's body having the paralysis. By way of non-limiting example, the training device may include a treadmill and a weight-bearing device configured to support at least a portion of the patient's body weight when the patient is positioned to use the treadmill. By way of another non-limiting example, the training device may include a device configured to bear at least a portion of the patient's body weight when the patient transitions between sitting and standing.

The selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit. The induced neurological signals are below the first stimulation threshold and insufficient to activate the at least one selected spinal circuit.

The method also includes applying electrical stimulation to a portion of a spinal cord of the patient. The electrical stimulation may be applied by an electrode array that is implanted epidurally in the spinal cord of the patient. Such an electrode array may be positioned at at least one of a lumbosacral region, a cervical region, and a thoracic region of the spinal cord. The electrical stimulation is below the second stimulation threshold such that the at least one selected spinal circuit is at least partially activatable by the addition of at least one of (a) a second portion of the induced neurological signals, and (b) supraspinal signals. While not a requirement, the first portion of the induced neurological signals may be the same as the second portion of the induced neurological signals. While also not a requirement, the electrical stimulation may not directly activate muscle cells in the portion of the patient's body having the paralysis. The electrical stimulation may include at least one of tonic stimulation and intermittent stimulation. The electrical stimulation may include simultaneous or sequential stimulation of different regions of the spinal cord.

If the paralysis was caused by a spinal cord injury at a first location along the spinal cord, the electrical stimulation may be applied by an electrode array that is implanted epidurally on the spinal cord of the patient at a second location below the first location along the spinal cord relative to the patient's brain.

Optionally, the method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-OHDPAT, Way 100.635, QUIPAZINE® (a 5-HT2A/C agonist), KETANSERIN® (a 5-HT2A/C antagonist), SR 57227A, ONDANSETRON® (a 5-HT3 antagonist), SB 269970, METHOXAMINE® (an α1 agonist), PRAZOSIN® (an α1 antagonist), CLONIDINE® (an α2 agonist), YOHIMBINE® (an α2 antagonist), SKF-81297, SCH-23390, QUINPIROLE® (a D2-like agonist), and ETICLOPRIDE® (a D2-like antagonist).

The electrical stimulation is defined by a set of parameter values, and activation of the selected spinal circuit may generate a quantifiable result. Optionally, the method may be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

Another exemplary embodiment is a method of enabling one or more functions selected from a group consisting of postural and/or locomotor activity, voluntary movement of leg position when not bearing weight, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using an electrode array while subjecting the subject to physical training that exposes the subject to relevant postural proprioceptive signals, locomotor proprioceptive signals, and supraspinal signals. At least one of the stimulation and physical training modulates in real time the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control (a) lower limbs; (b) upper limbs; (c) the subject's bladder; and/or (d) the subject's bowel. The physical training may include standing, stepping, sitting down, laying down, reaching, grasping, stabilizing sitting posture, and/or stabilizing standing posture.

The electrode array may include one or more electrodes stimulated in a monopolar configuration and/or one or more electrodes stimulated in a bipolar configuration. The electrode array includes a plurality of electrodes that may have an interelectrode spacing between adjacent electrodes of about 500 µm to about 1.5 mm. The electrode array may be an epidurally implanted electrode array. Such an epidurally implanted electrode array may be placed over at least one of a lumbosacral portion of the spinal cord, a thoracic portion of the spinal cord, and a cervical portion of the spinal cord.

The stimulation may include tonic stimulation and/or intermittent stimulation. The stimulation may include simultaneous or sequential stimulation of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

Another exemplary embodiment is a method that includes implanting an electrode array on the patient's spinal cord, positioning the patient in a training device configured to assist with physical training that is configured to induce neurological signals in the portion of the patient's body having the paralysis, and applying electrical stimulation to a portion of a spinal cord of the patient. The induced neurological signals is below the first stimulation threshold and insufficient to activate the at least one selected spinal circuit. The electrical stimulation is below the second stimulation threshold such that the at least one selected spinal circuit is at least partially activatable by the addition of at least one of (a) a second portion of the induced neurological signals, and (b) supraspinal signals. Optionally, the electrode array may be implanted on the dura of the patient's spinal cord.

Another exemplary embodiment is a system that includes a training device configured to assist with physically training of the patient, an implantable electrode array configured to be implanted on the dura of the patient's spinal cord, a stimulation generator connected to the implantable electrode array. When undertaken, the physical training induces neurological signals in the portion of the patient's body having the paralysis. The stimulation generator is configured to apply electrical stimulation to the implantable electrode array. Electrophysiological properties of at least one spinal circuit in the patient's spinal cord is modulated by the electrical stimulation and at least one of (1) a first portion of the induced neurological signals and (2) supraspinal signals such that the at least one spinal circuit is at least partially activatable by at least one of (a) the supraspinal signals and (b) a second portion of the induced neurological signals. The induced neurological signals and supraspinal signals are below the first stimulation threshold and insufficient to activate the at least one selected spinal circuit, and the electrical stimulation applied to the implantable electrode array is below the second stimulation threshold.

Another exemplary embodiment is a system that includes means for physically training the patient to induce neurological signals in the portion of the patient's body having the paralysis, and means for applying electrical stimulation to a portion of a spinal cord of the patient. Electrophysiological properties of at least one spinal circuit in the patient's spinal cord being modulated by the electrical stimulation and at least one of a first portion of the induced neurological signals and supraspinal signals such that the at least one spinal circuit is at least partially activatable by at least one of (a) the supraspinal signals and (b) a second portion of the induced neurological signals.

BRIEF DESCRIPTION OF THE SEVERAL VIEWS OF THE DRAWING(S)

FIG. 1 summarizes recent experiments in rats that were carried out to assess the effectiveness of epidural stimulation coupled with combined drug therapy in the treatment of complete spinal cord injuries. The combination of QUIPAZINE and 8-OHDPAT with simultaneous epidural stimulation at spinal sites L2 and S1 results in robust coordinated stepping as early as one week after a complete spinal cord transection. Locomotor behavior observed from a typical rat before the injury and one week after a complete midthoracic spinal cord transection. The amount of body weight support provided to the rat is shown in red. One week post-injury, no spontaneous stepping activity is observed. Administration of QUIPAZINE (a $5\text{-HT}_2$ receptor agonist) and 8-OHDPAT (a $5\text{-HT}_{1/7}$ receptor agonist) results in erratic movements. Epidural stimulation simultaneously at L2 plus S1 in combination with either QUIPAZINE or 8-OHDPAT enables plantar stepping. The combination of epidural stimulation at L2 plus S1 with the administration of QUIPAZINE plus 8-OHDPAT clearly has a synergistic effect, resulting in coordinated, plantar stepping with features resembling those observed pre-lesion. Sol, soleus; TA, tibialis anterior;MTP, metatarsal-phalangeal.

FIG. 2 illustrates step training with epidural stimulation at both L2 and S1 spinal sites in combination with use of QUIPAZINE and 8-OHDAPT (5-HT agonists) prevents degradation of neuronal function and promotes improvement of the stepping ability of spinal rats transected as adults. From top to bottom: Representative stick diagrams of left and right hindlimb movements during gait swing phase, recorded 8 weeks post-injury. The successive trajectories of the left and right limb endpoint (MTP) during a 10 s stepping sequence are shown. Blue, red, and black trajectories represent stance, drag, and swing phases. The gait diagrams reconstructed from the displacement of the left and right hindlimbs during stepping are displayed conjointly with the EMG activity of left and right soleus ("Sol") and tibialis anterior ("TA") muscles. Compared to a rat with no rehabilitation, the rat that received step training every other day for 7 weeks shows consistent hindlimb movements, coordination between the left and right sides, and increased recruitment of both extensor and flexor leg muscles.

FIG. 3 shows a photograph of an illustrative 1st generation high density epidural stimulating array comprising 10 electrodes.

FIG. 4 shows a schematic diagram of an illustrative laminectomy procedure for placing an epidural stimulating array over the lumbosacral spinal cord.

FIG. 5 panels A-D illustrates results for site-specific selective muscle activation. The extensor digitorum longus (EDL, panel A), vastus lateralis (VL, panel B), and tibialis anterior (TA, panel C) muscles were selectively activated using low-current stimulation at specific spinal sites. Preferential activation of the medial gastrocnemius (MG, panel D) muscle also was obtained, but occurred with co-activation of the VL. Data represent normalized peak-to-peak amplitudes of 10 averaged responses.

Figure 6:
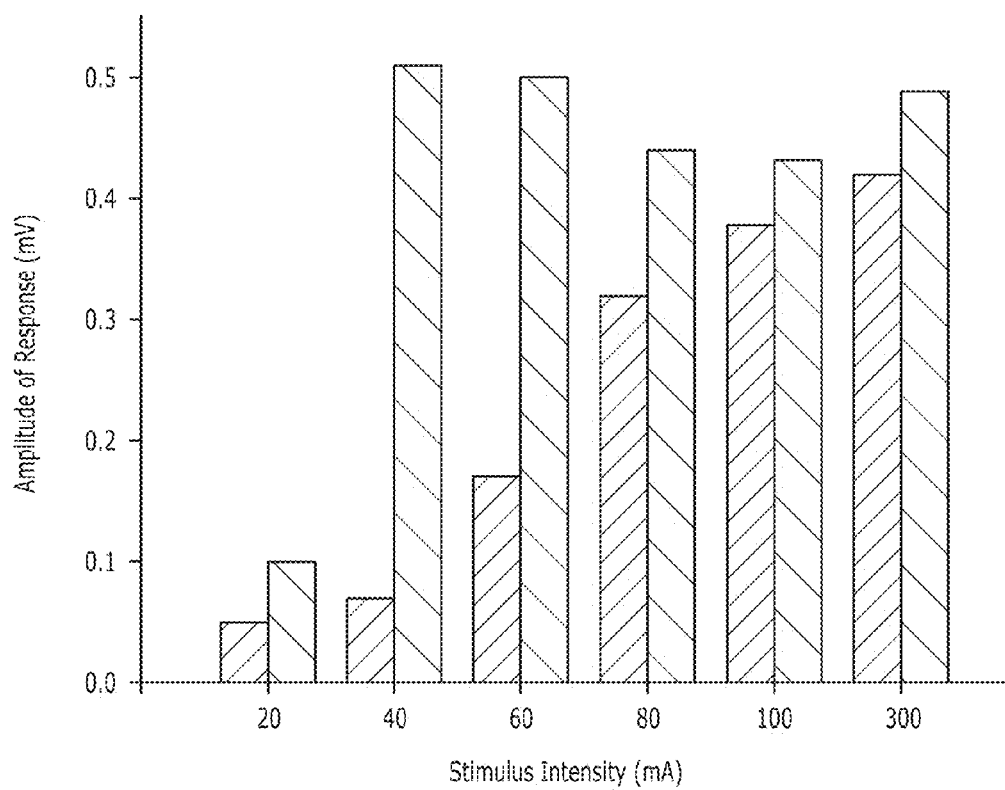

FIG. 6 shows that interelectrode distance modulates muscle recruitment. Using a smaller spacing (1500 μm, filled bars) bipolar configuration, graded muscle activation was achieved. With larger spacing (4500 μm, unfilled bars), approaching a monopolar configuration, a muscle quickly attained maximal activation at low currents. Thus, the specific goal and sensitivity requirements of a particular motor task may dictate optimal interelectrode spacing and whether a monopolar or bipolar configuration is chosen.

Figure 7:
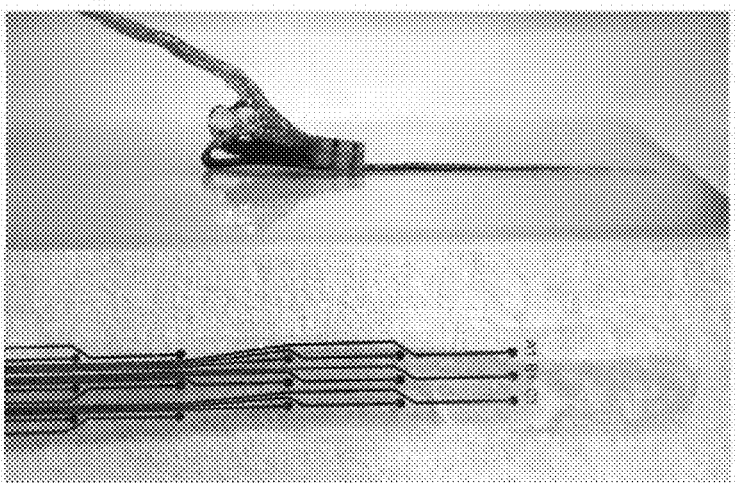

FIG. 7 shows a photograph of an illustrative 27 electrode rat epidural stimulation array (in a 9×3 configuration), including head-connector.

Figure 8:
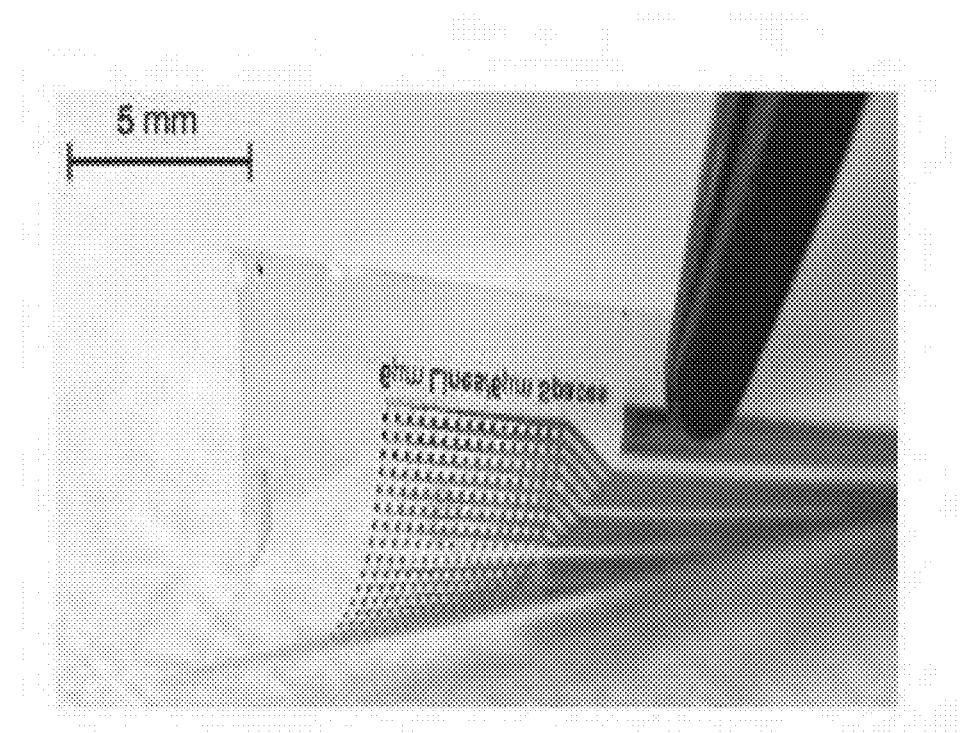

FIG. 8 shows a photograph of an illustrative 256 electrode array.

Figure 9:
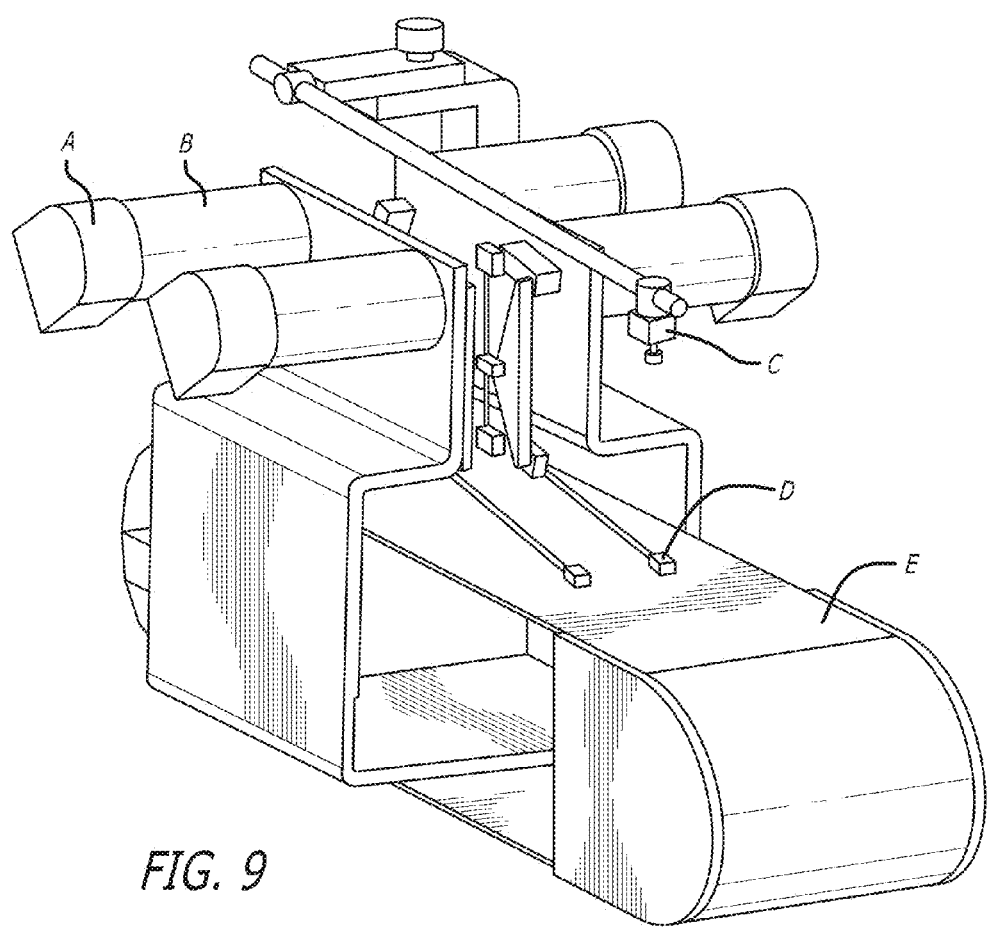

FIG. 9 illustrates a schematic of a step training robot. Illustrative components include: A) Optical encoder; B) Motor; C) Weight support; D) Manipulators; and E) Motorized treadmill.

Figures 10A, 10B:

FIGS. 10A and 10B show radiographic and clinical characteristics of an individual with motor complete, but sensory incomplete SCI. FIG. 10A: T2 weighted sagittal Magnetic Resonance Image of cervical spine at subject's injury site (C7-T1). Hyperintensity and myelomalacia noted at site of injury. FIG. 10B: AIS evaluation of the subject.

Figure 11A:
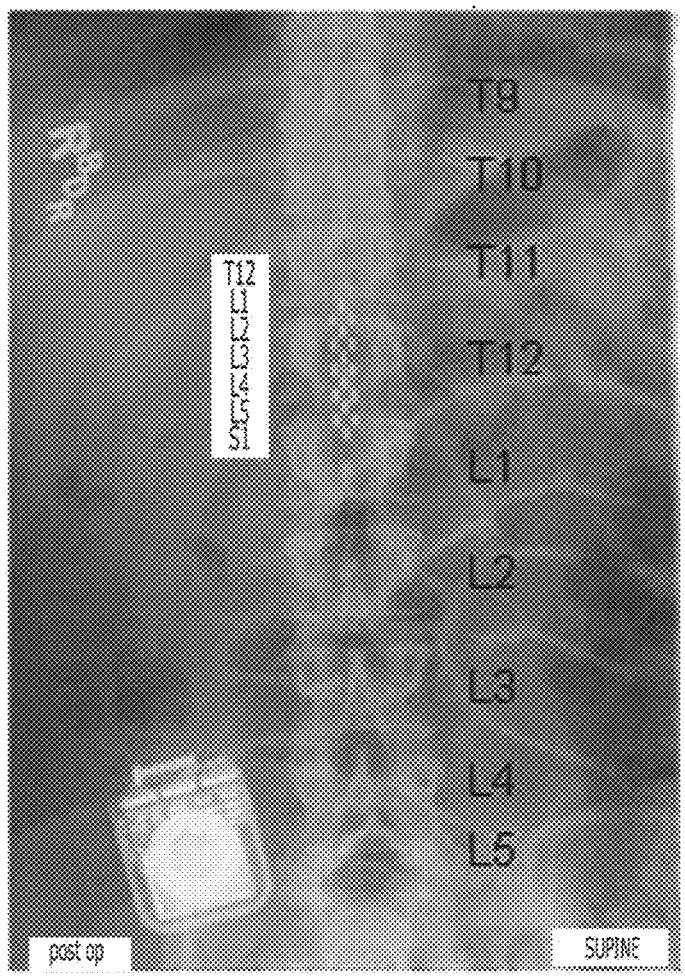
Figure 11B:
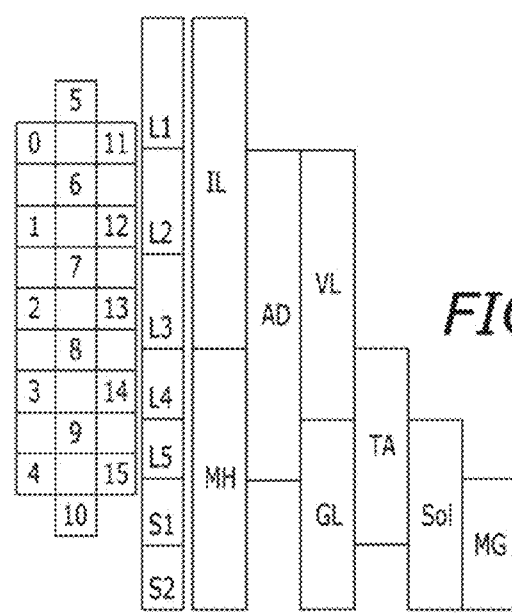
Figure 11C:
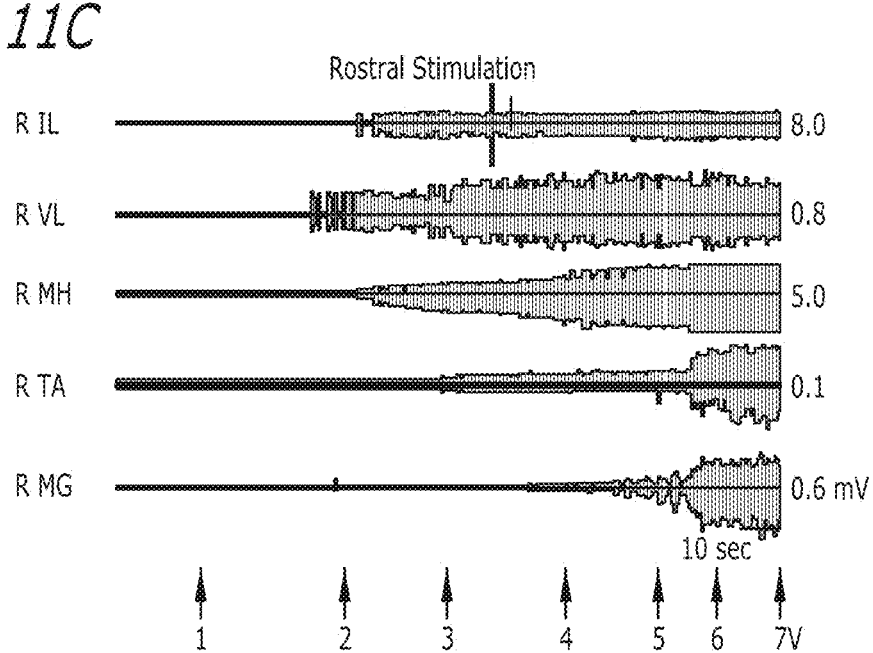
Figure 11D:
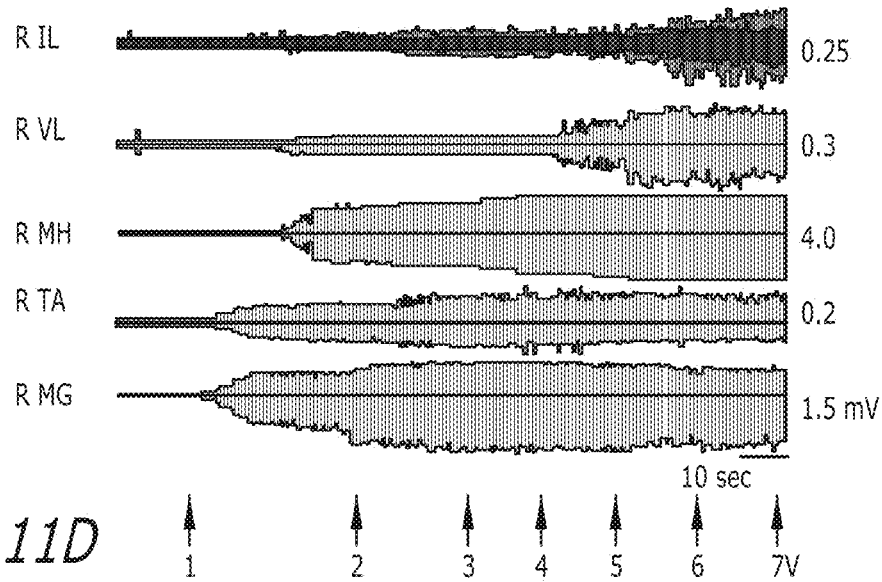

FIGS. 11A-11D illustrate localization of electrode array relative to motoneuron pools as identified with motor evoked potentials during surgical implantation. The voltage thresholds for evoked potentials of proximal muscles are lower when stimulating the more rostral electrodes. The voltage thresholds for motor evoked potentials of the distal muscles are lower when stimulating the caudal electrodes. FIG. 11A: Post-operative fluoroscopy of the thoracolumbar spine showing the location of the implanted electrode array and neurostimulator. FIG. 11B: Depiction of 16-electrode array configuration relative to spinal dorsal roots and corresponding motoneuron pools identified using EMG recorded from leg muscles. FIGS. 11C and 11D: Motor evoked potentials elicited using epidural stimulation at 2 Hz, 210 μs from 0.0 to 7 V with rostral electrodes, (5−: 6+) and caudal electrodes (10−: 9+) respectively. Muscles: IL: iliopsoas, AD: adductor magnus, VL: vastus lateralis, MH: medial hamstrings, TA: tibialis anterior, GL: gluteus maximus, SL: soleus, MG: medial gastrocnemius.

Figure 12:
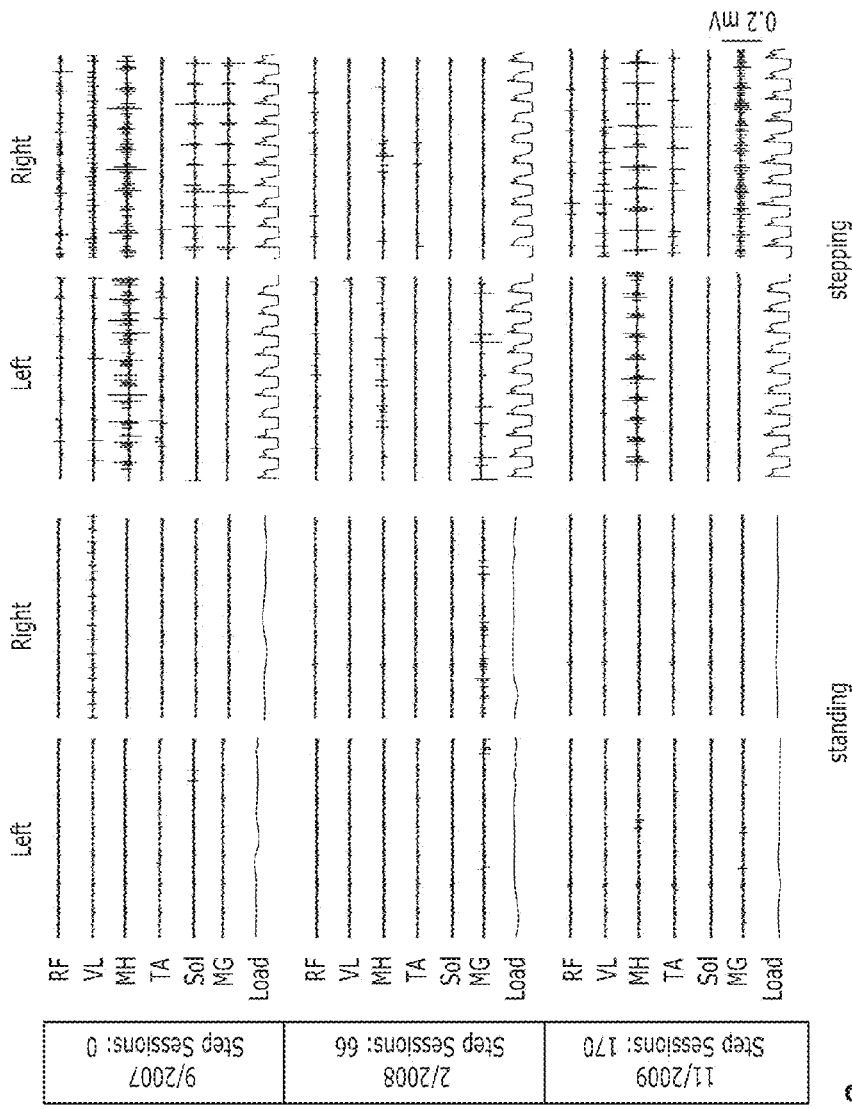

FIG. 12 illustrates lower extremity EMG activity during standing with BWST (panel A), and stepping with body weight support ("BWST") (panel B). Three different time points over a two-year period and 170 training sessions showed no change in the EMG pattern during standing or stepping.

Figures 13A, 13B:
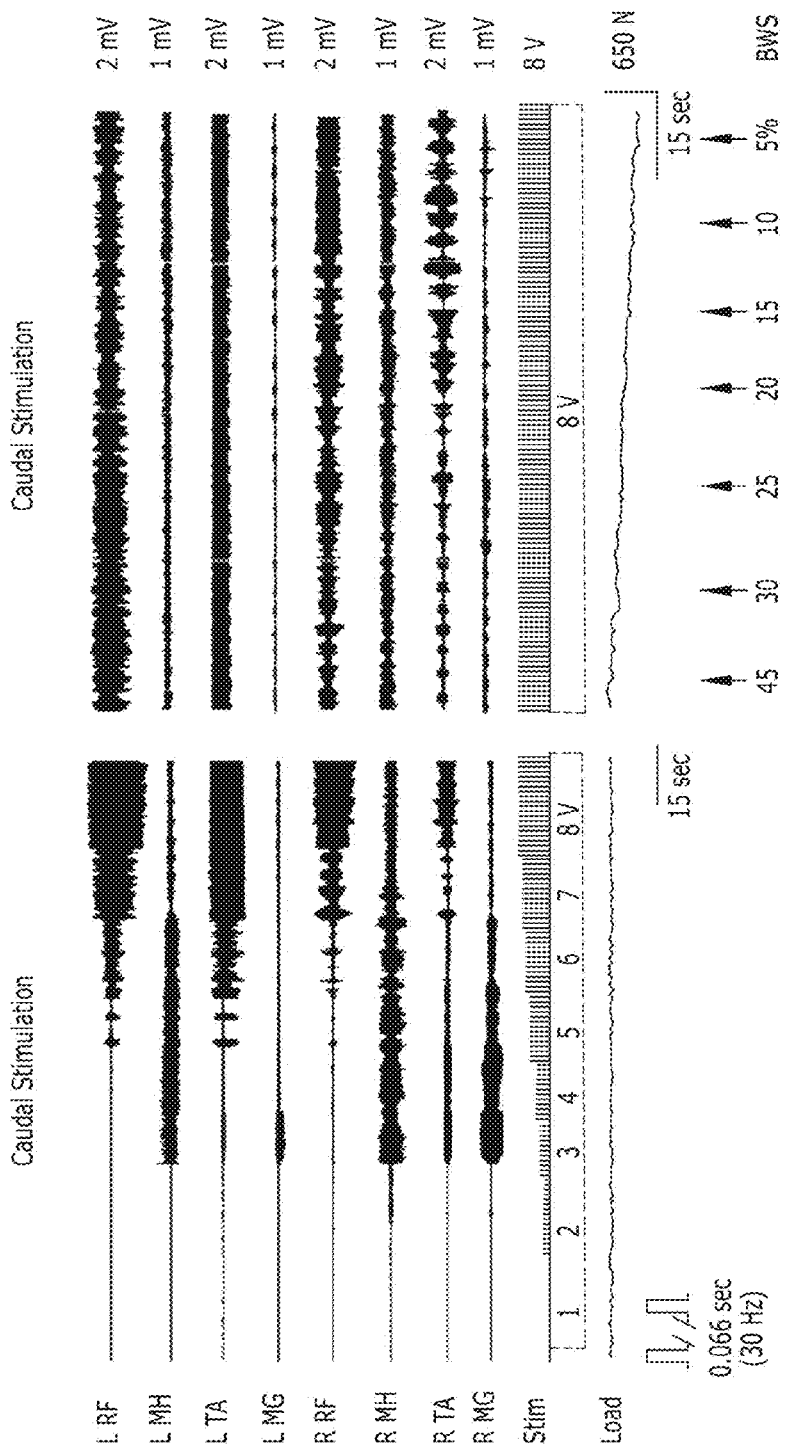

FIGS. 13A-13B show EMG activity with epidural stimulation during independent standing. These data demonstrate that the output of the spinal circuitry can be sufficiently modulated by the proprioceptive input to sustain independent stepping. EMG activity increases in amplitude and becomes more constant bilaterally in most muscles with independent standing occurring at 8 V. Reducing BWS changed the EMG amplitudes and oscillatory patterns differently among muscles. EMG activity during standing with BWS and with epidural stimulation (15 Hz) of caudal lumbosacral segments (4/10/15−: 3/9+) (panel A) from 1-8V and 65% BWS and (panel B) at 8V while reducing the BWS from 45% to 5%. Muscle: rectus femoris (RF), medial hamstrings (MH), tibialis anterior (TA), and medial gastrocnemius (MG). Left (L) and right (R).

Figure 14E:
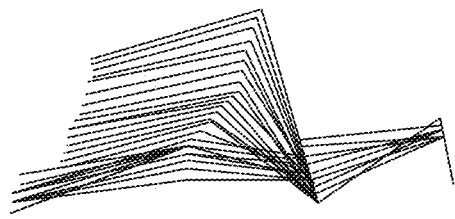
Figure 14D:
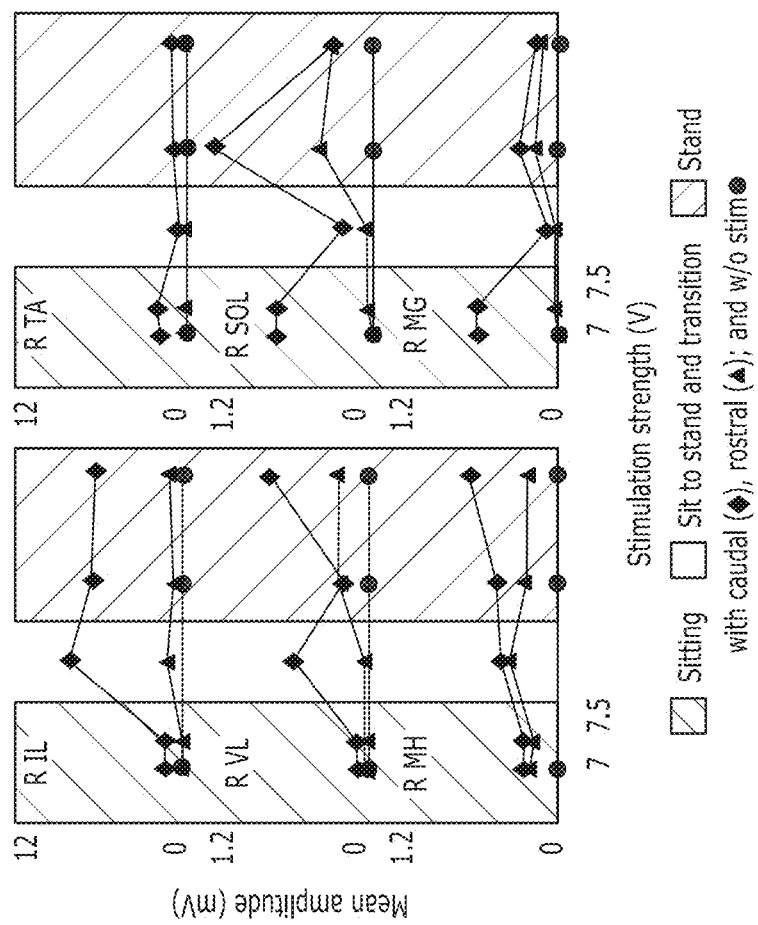

FIGS. 14A-14-E illustrate lower extremity EMG activity during sitting and standing with and without epidural stimulation. There was little or no EMG activity without stimulation, but with epidural stimulation there was significant EMG activity that was modulated during the transition from sitting to standing. Panel A: EMG activity during sitting (green) and standing (yellow) with no epidural stimulation. Panel B: EMG activity during sitting (green) and standing (yellow) with 4V to 7.5 V, 15 Hz stimulation of the rostral lumbar segments (0/5/11−: 1/6/12+). Panel C: EMG activity during sitting (green) and standing (yellow) with epidural stimulation (15 Hz) of the caudal lumbosacral segments (4/10/15−: 3/9/14+). Panel D: Averaged mean amplitude (mV) of right side motor evoked responses during sitting and standing elicited from epidural stimulation (b) or rostal stimulation is represented by "▲," (c) or caudal stimulation is represented by "♦," and no stimulation is represented by opened circles (o). No stimulation values are only shown for sitting and standing. Panel E: Kinematic representation of transition from sitting to standing with caudal stimulation. Muscles: iliopsoas (IL), vastus lateralis (VL), medial hamstrings (MH), tibialis anterior (TA), soleus (Sol), and medial gastrocnemius (MO). Left side muscles (L), right side muscles (R).

Figure 15A:
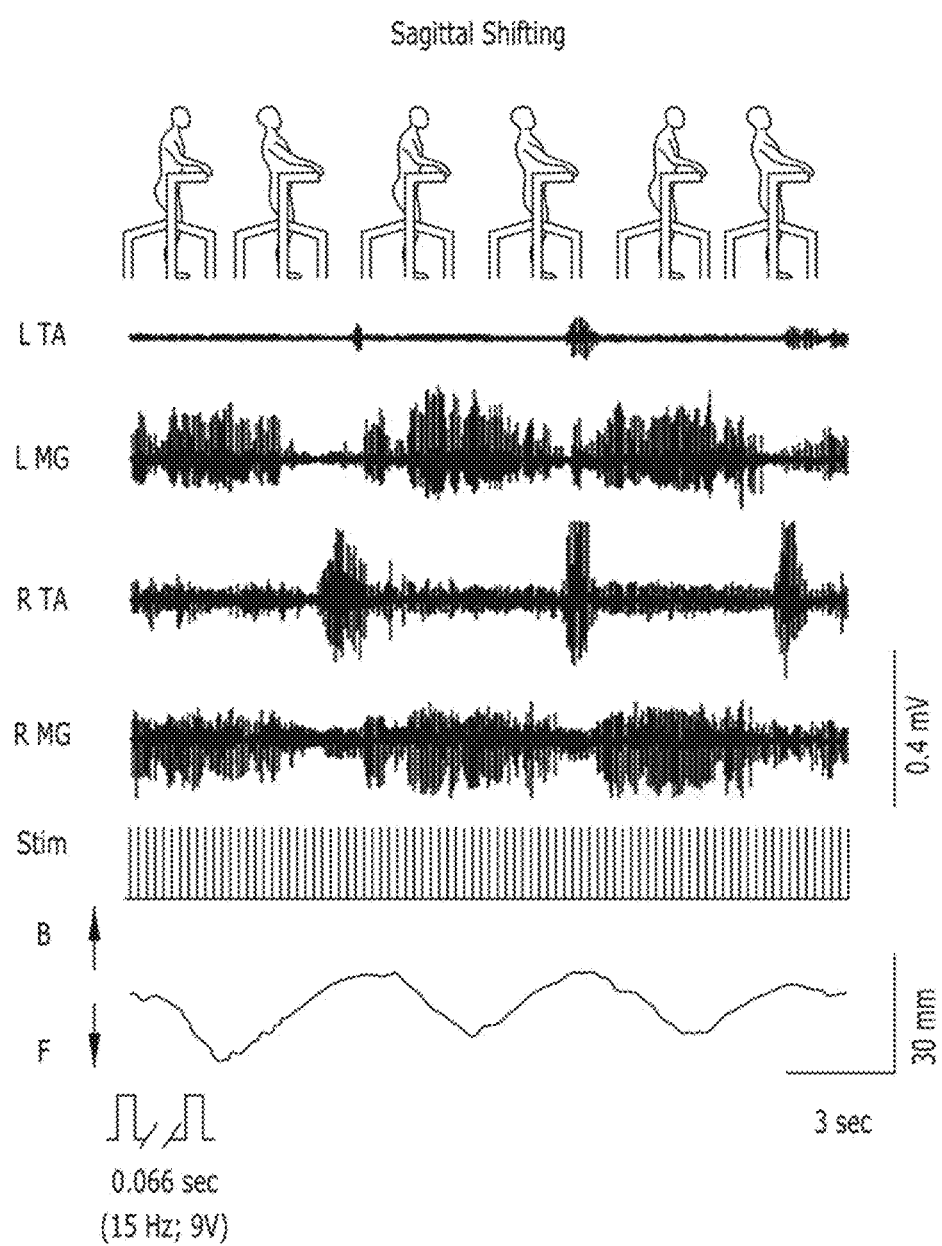
Figure 15B:
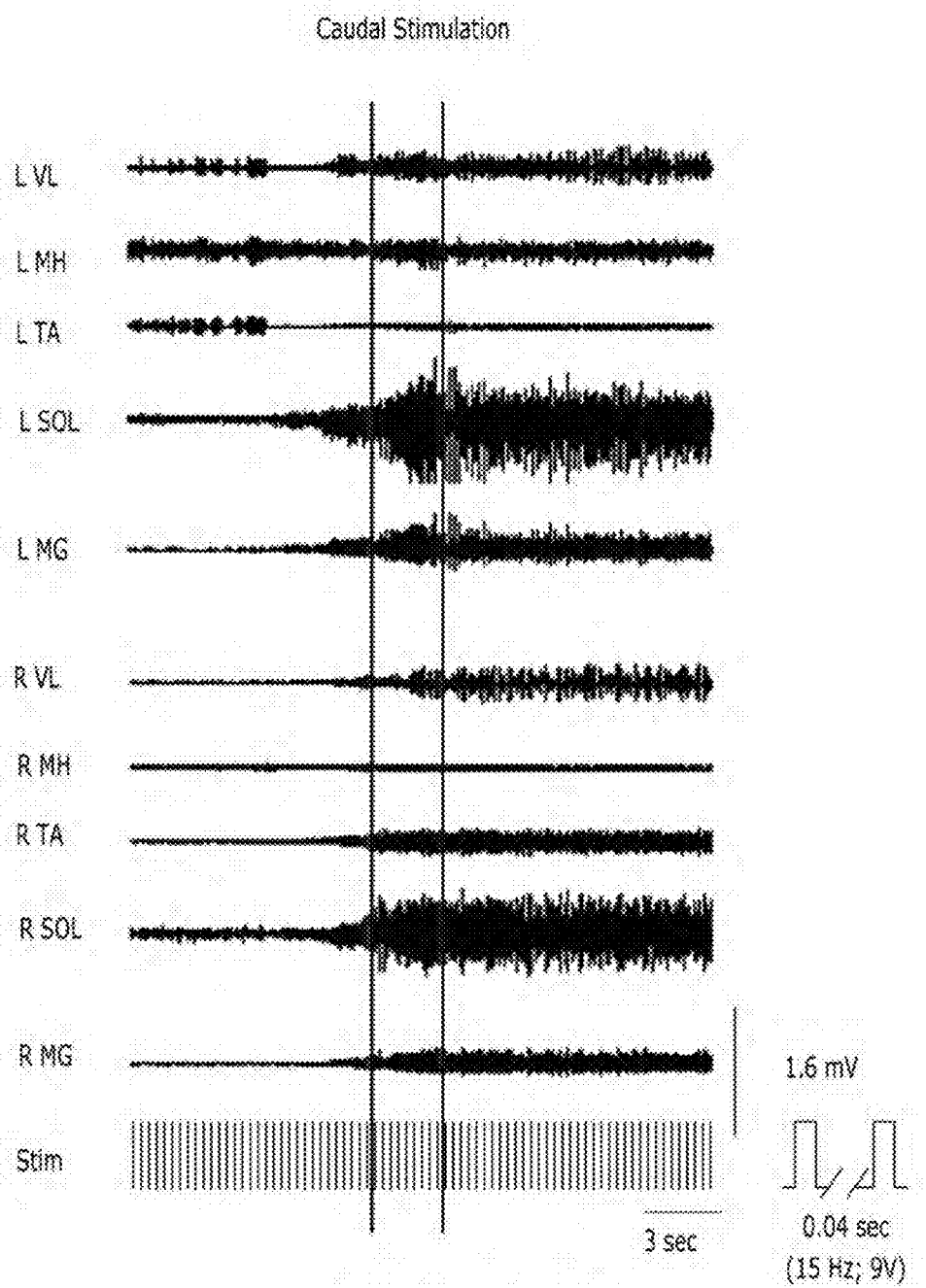
Figures 16A, 16B:
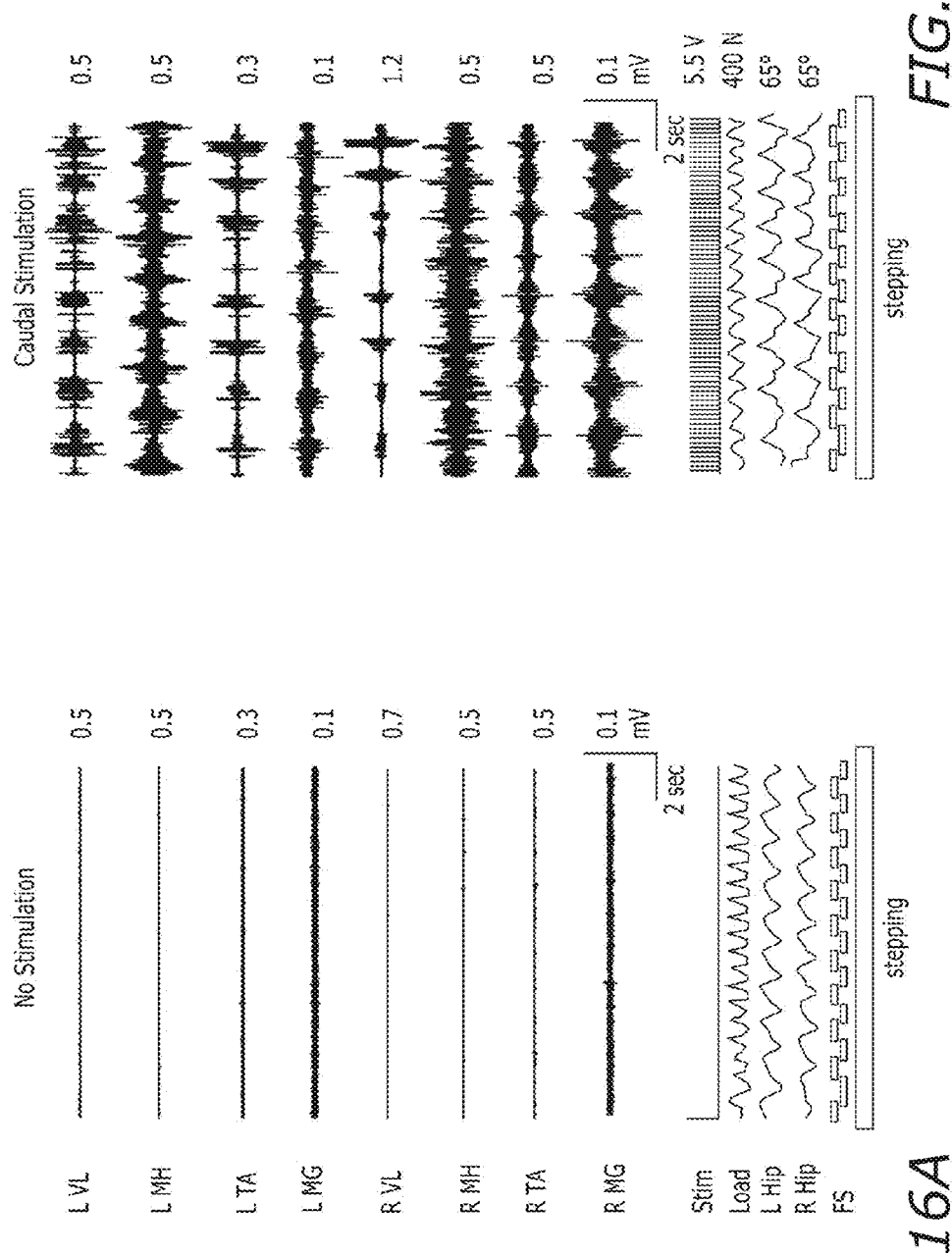
Figures 16C, 16D:
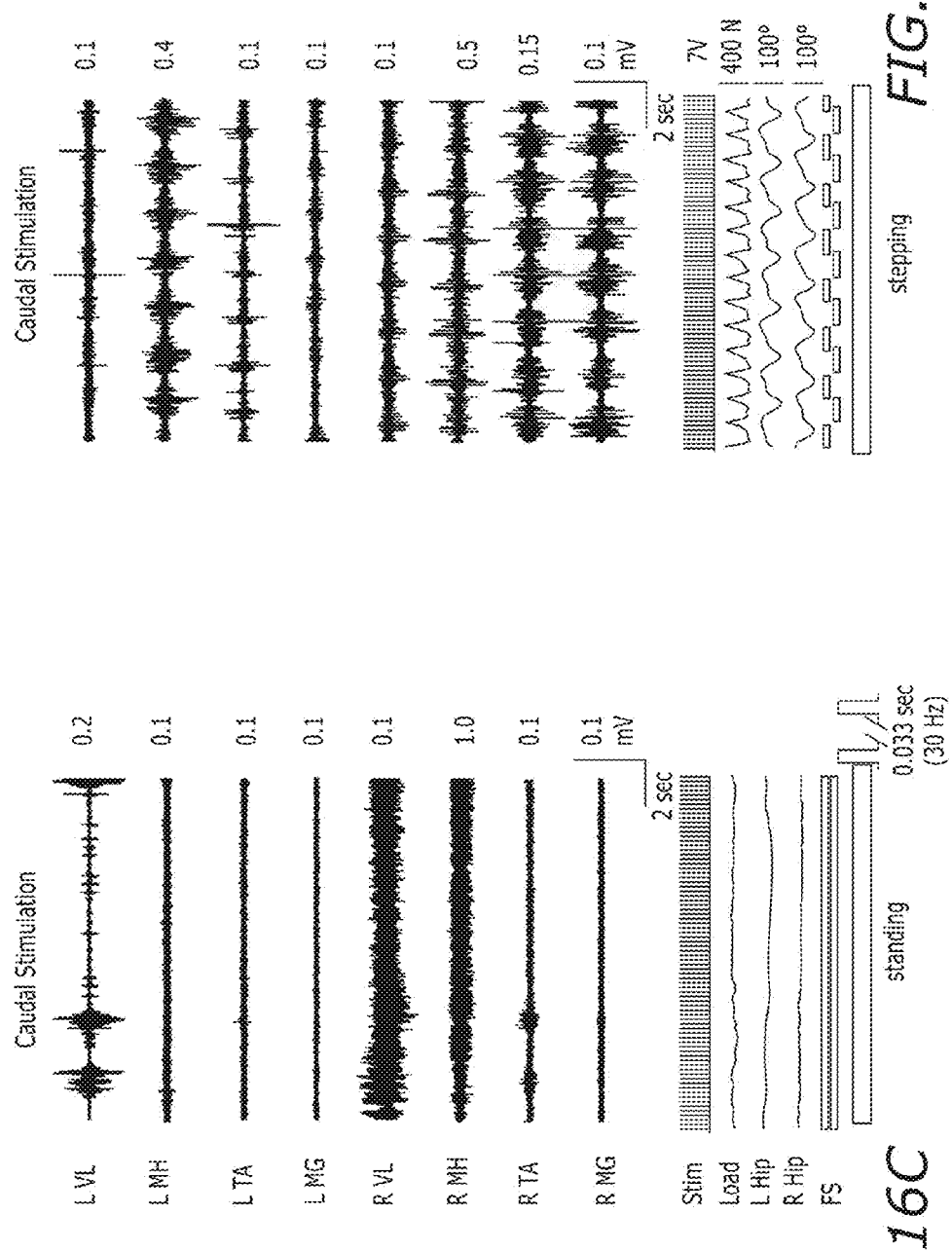

FIGS. 15A-15B illustrate EMG activity with epidural stimulation during independent standing. Panel A: EMG activity with epidural stimulation (8 V, 15 Hz) of the caudal lumbosacral segments (4/10/15−: 3/9/14+) during weight shifting. Body movements are depicted in the top panel as displacement of the center of gravity (CGX) lateral shifting (CGY) to the right (R)) and left (L) sides in the bottom panels. Panel B: EMG activity with epidural stimulation during independent standing. Interpulse interval depicting stimulation frequency is shown on the lower right of the top and bottom graphs. Red line indicates initiation of independent standing as subject counted backwards from 3, blue line indicates when independent standing was obtained. Muscle: iliopsoas (IL), rectus femoris (RF), medial hamstrings (MH), tibialis anterior (TA), Soleus (SOL) and medial gastrocnemius (MG). Left (L) and right (R).

FIGS. 16A-16D show lower extremity EMG activity during standing and stepping with body weight support and manual facilitation with and without epidural stimulation of caudal lumbosacral segments. The EMG patterns were modified by the intensity of stimulation and by different patterns of sensory input. EMG activity during stepping (50% BWS, 1.07 m/s) (panel A) without stimulation and (panel B) (45% BWS, 0.8 m/s) with epidural stimulation (5.5 V, 30 Hz) of caudal lumbosacral segments (4/10/15−: 3/9+). EMG activity during (panel C) standing (25% BWS) and (panels B, D) stepping (50% BWS, 1.07 m/s) with epidural stimulation (7.0 V, 30 Hz) of caudal lumbosacral segments (4/10/15−: 3/9+) (panel C). For stepping (panels B, C, and D) data were selected from 5 consecutive cycles. Muscles: vastus lateralis (VL), medial hamstrings (MH), tibialis anterior (TA), and medial gastrocnemius (MG). Left (L) and right (R) side muscles. Load is load cell reading in Newtons (N). Left (LHip) and Right (RHip) are sagittal joint angles for the hip joint. Left (LFS) and right (RFS) footswitches reflect stance phase.

Figure 17A:
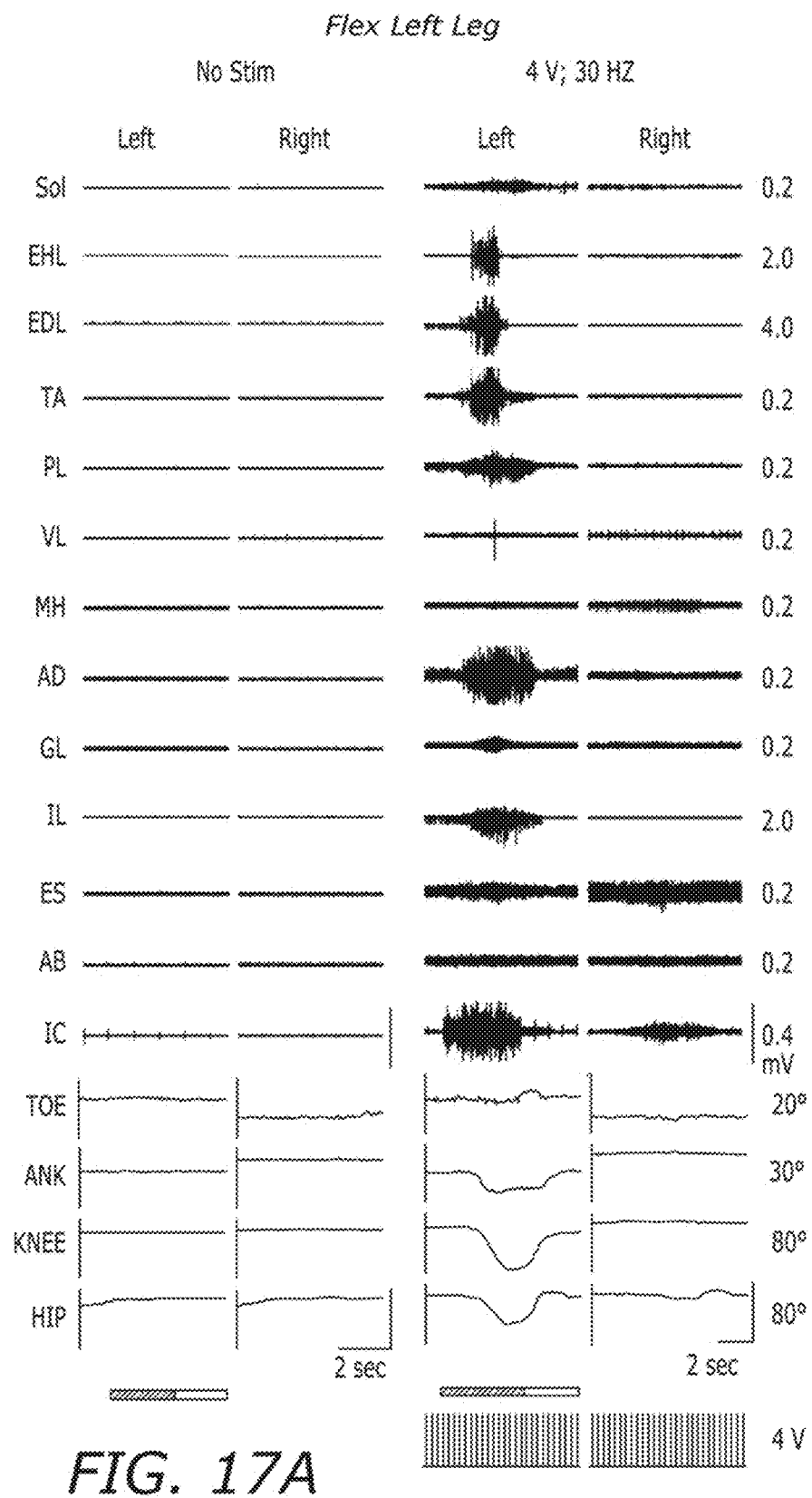
Figure 17B:
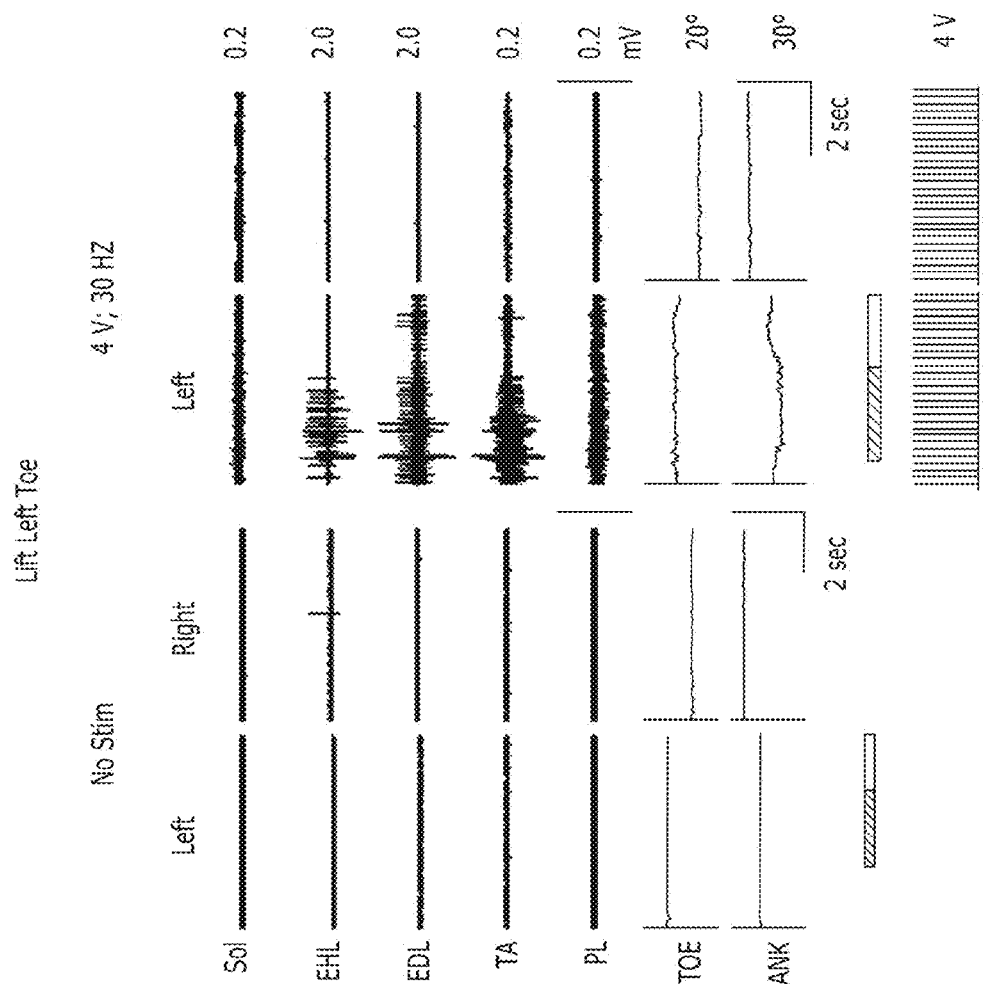
Figure 17C:
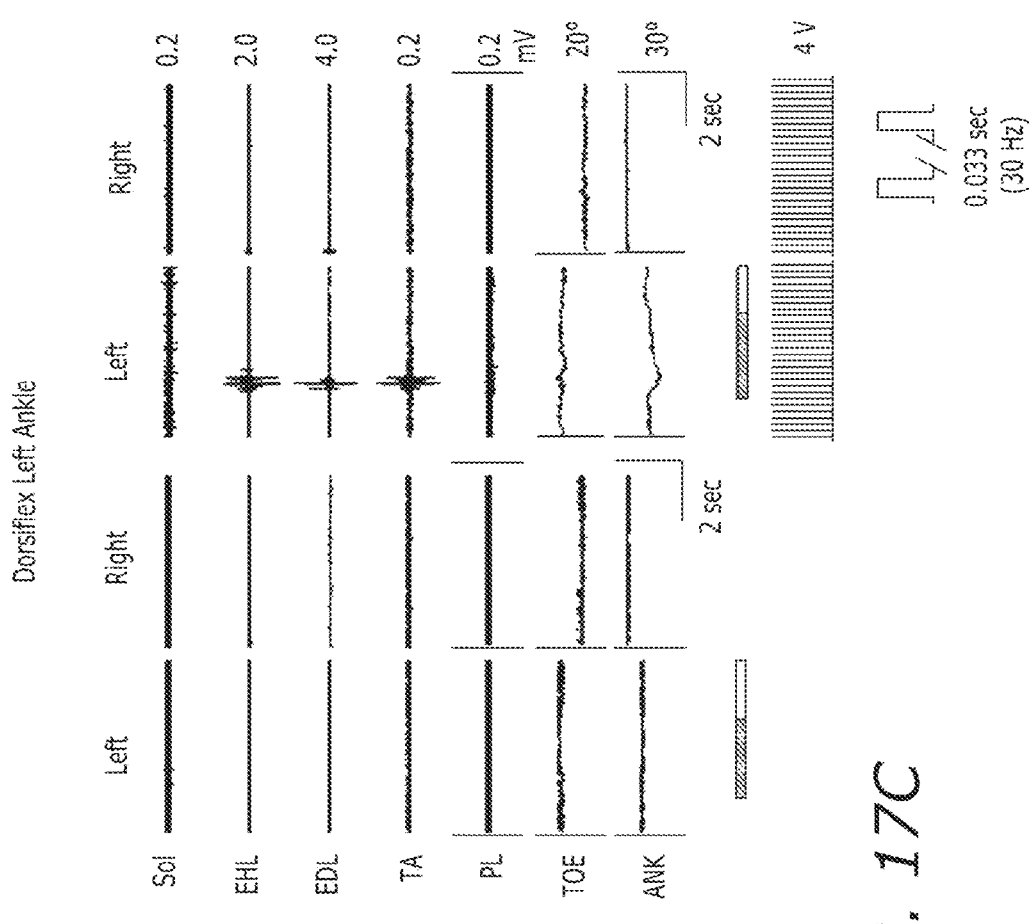

FIGS. 17A-17E show lower extremity EMG activity during voluntary control in a supine position with and without stimulation. The black bar indicates the command to generate flexion and move the left leg up (FIG. 17A), left ankle dorsiflexion (FIG. 17B), and left toe extension (FIG. 17C), and the white bar indicates the command to relax the leg. Left and right sides are shown to emphasize the isolated control of the left side following the command. The right and left intercostals (IC) are activated during the voluntary attempt of the leg, as the subject inhales as he attempts to perform the movement. Muscles: soleus (SOL), extensor digitorum longus (EDL), extensor hallucis longus (EHL), tibialis anterior (TA), peroneus longus (PL), vastus lateralis (VL), medial hamstrings (MH), adductor magnus (AD), gluteus maximus (GL), iliopsoas (IL), erector spinae (ES), rectus abdominus (AB), intercostals (IC). Sagittal joint angles for the toe (1st metatarsal relative to foot), ankle, knee, and hip joints. FIG. 17D: Stick figures were generated from the kinematics during the up and down commands for both trials with and without epidural stimulation. FIG. 17E: Relationship between onset (solid)/offset (open) of EMG burst for TA muscle and command up/down. Three trials were performed for the toe and leg voluntary movements and two trials for the ankle. All commands were given to move the left leg. The dotted line represents the line of identity (x=y).

Figure 18A:
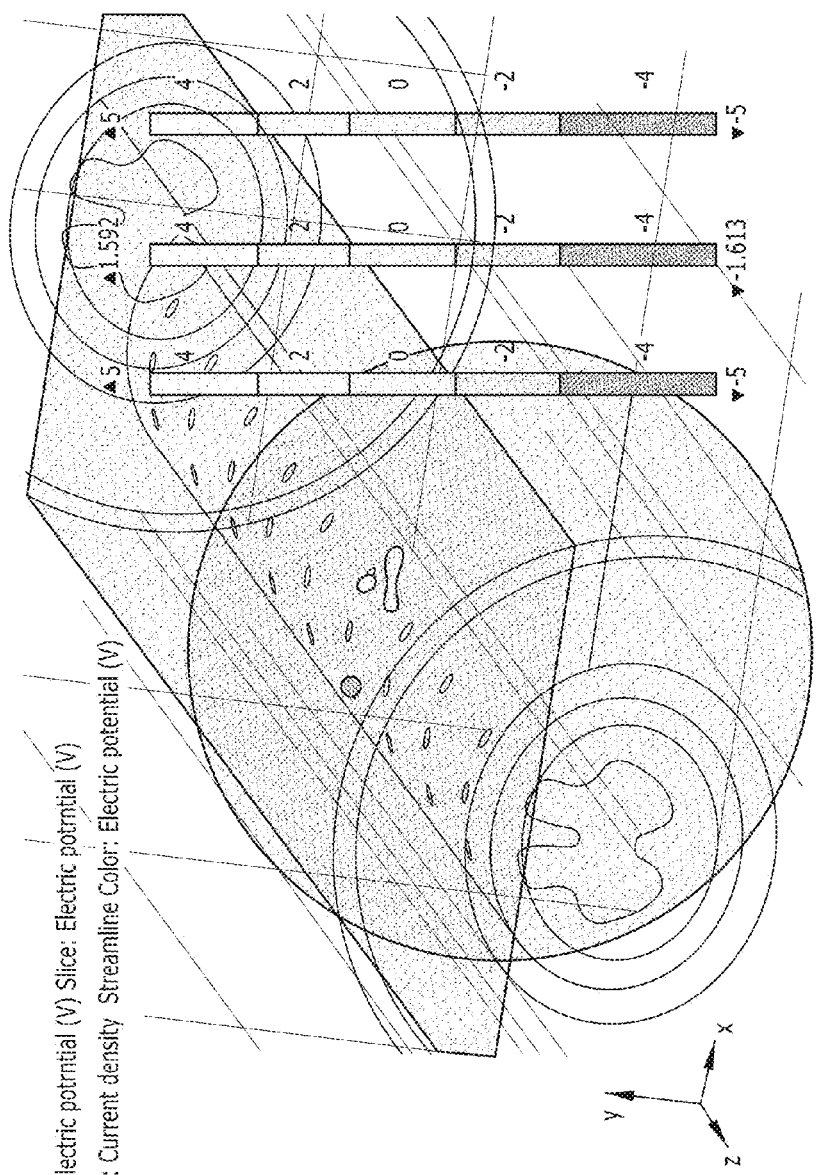

FIG. 18A shows a 3D view of epidural spinal electrode (with 2 of 27 electrodes activated) placed in the epidural space of a simulated spinal cord.

Figure 18B:
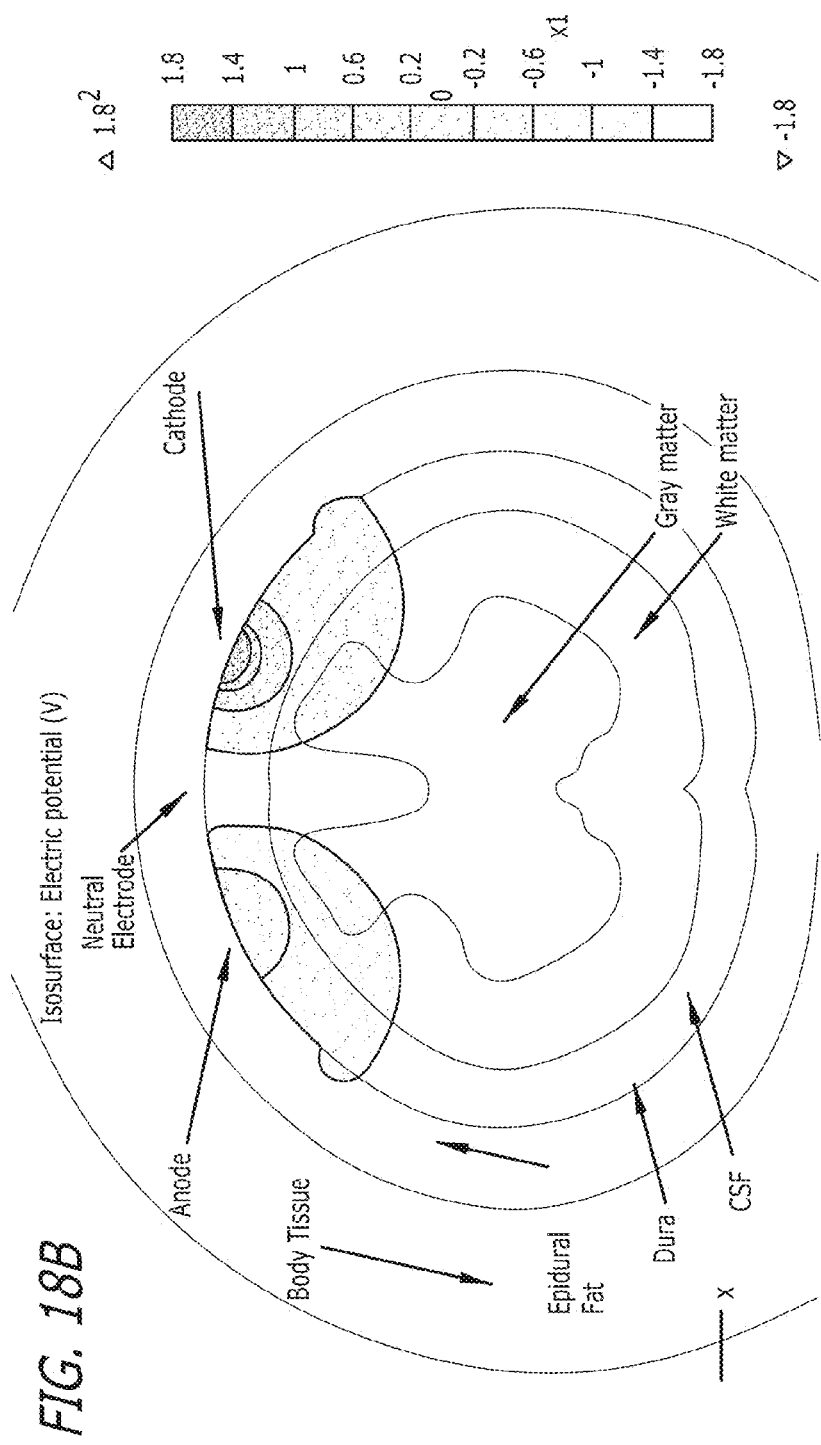

FIG. 18B shows isopotential contours of electrical field (in slice through center of bipolarly activated electrodes). Model compartments include gray matter, white matter, CSF, epidural fat, and surrounding body tissue.

Figure 19:
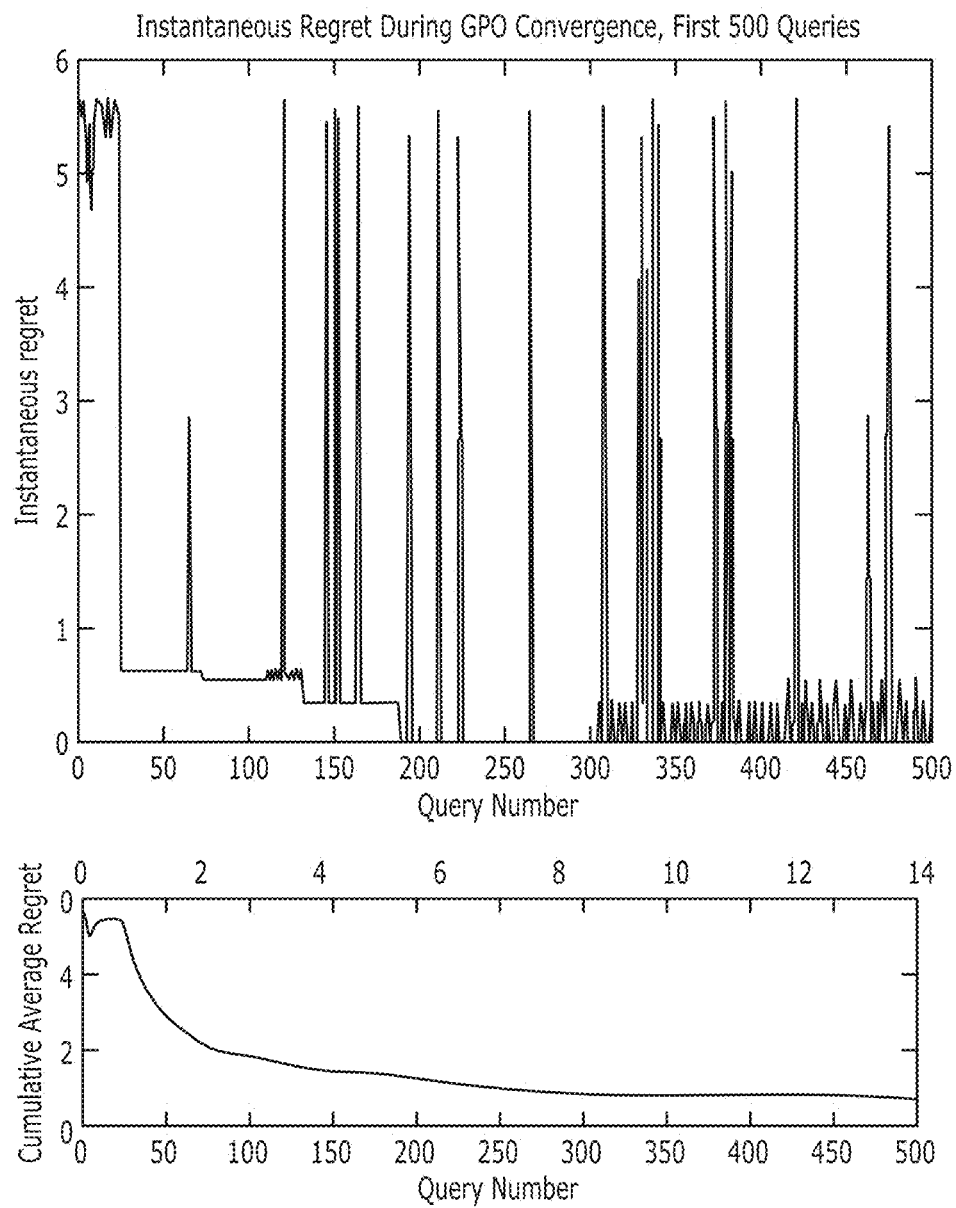

FIG. 19 (top) shows instantaneous regret (a measure of machine learning error) vs. learning iteration (labeled as "query number") for Gaussian Process Optimization of array stimulation parameters in the simulated spinal cord of FIGS. 18A and 18B. The "bursts" of poor performance corresponds to excursions of the learning algorithm to regions of parameter space that are previously unexplored, but which are found to have poor performance. FIG. 19 (bottom) shows the average cumulative regret vs. learning iteration. The average cumulative regret is a smoothed version of the regret performance function which better shows the algorithm's overall progress in selecting optimal stimulation parameters.

DETAILED DESCRIPTION OF THE INVENTION

Unless defined otherwise, technical and scientific terms used herein have the same meaning as commonly understood by one of ordinary skill in the art to which this invention belongs.

The term "motor complete" when used with respect to a spinal cord injury indicates that there is no motor function below the lesion, (e.g., no movement can be voluntarily induced in muscles innervated by spinal segments below the spinal lesion (e.g., as described below in Example 1).

The term "bipolar stimulation" refers to stimulation between two closely spaced electrodes.

The term "monopolar stimulation" refers to stimulation between a local electrode and a common distant return electrode.

The term "autonomic function" refers to functions controlled by the peripheral nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

The term "cognitive function" refers to awareness of one's surrounding environment and the ability to function effectively, behaviorally, and mentally in a given environment.

In various embodiments, methods, devices, and optional pharmacological agents are provided to facilitate movement in a mammalian subject (e.g., a human) having spinal cord injury, brain injury, or other neurological disease or injury. In certain embodiments, the methods involve stimulating the spinal cord of the subject using an electrode array where the stimulation modulates the electrophysiological properties of selected spinal circuits in the subject so they can be activated by proprioceptive derived information and/or input from supraspinal. In various embodiments, the stimulation is typically accompanied by physical training (e.g., movement) of the region where the sensory-motor circuits of the spinal cord are located.

In particular illustrative embodiments, the devices, optional pharmacological agents, and methods described herein stimulate the spinal cord with, e.g., electrode arrays, that modulate the proprioceptive and supraspinal information which controls the lower limbs during standing and/or stepping and/or the upper limbs during reaching and/or grasping conditions. It is the sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices, optional pharmacological agents, and methods described herein exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

In one illustrative embodiment, the subject is fitted with one or more implantable electrode arrays that afford selective stimulation and control capability to select sites, mode(s), and intensity of stimulation via electrodes placed epidurally over, for example, the lumbosacral spinal cord and/or cervical spinal cord to facilitate movement of the arms and/or legs of individuals with a severely debilitating neuromotor disorder.

The subject receives the implant (a standard procedure when used for pain alleviation), and typically about two weeks post implant, the subject is tested to identify the most effective subject specific stimulation paradigms for facilitation of movement (e.g., stepping and standing and/or arm and/or hand movement). Using these stimulation paradigms, the subject practices standing and stepping and/or reaching or grabbing in an interactive rehabilitation program while being subject to spinal stimulation.

Depending on the site/type of injury and the locomotor activity it is desired to facilitate, particular spinal stimulation protocols include, but are not limited to specific stimulation sites along the lumbosacral and/or cervical spinal cord; specific combinations of stimulation sites along the lumbosacral and/or cervical spinal cord; specific stimulation amplitudes; specific stimulation polarities (e.g., monopolar and bipolar stimulation modalities); specific stimulation frequencies; and/or specific stimulation pulse widths.

In various embodiments, the system is designed so that the patient can use and control it in the home environment.

In various embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, as demonstrated in Example 1 (described below), the methods and devices described herein are effective in a spinal cord injured subject that is clinically classified as motor complete; that is, there is no motor function below the lesion. In various embodiments, the specific combination of electrodes activated/stimulated within an array and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

The approach described herein can provide some basic postural, locomotor and reaching and grasping patterns on their own. However, they are also likely to be a building block for future recovery strategies. Based on certain successes in animals and some preliminary human studies (see below), it appears that a strategy combining effective epidural stimulation of the appropriate spinal circuits with physical rehabilitation and pharmacological intervention can provide practical therapies for complete SCI human patients. There is sufficient evidence from our work that such an approach should be enough to enable weight bearing standing, stepping and/or reaching or grasping. Such capability can give complete SCI patients the ability to participate in exercise, which is known to be highly beneficial for their physical and mental health. We also expect our method should enable movement with the aid of assistive walkers. While far from complete recovery of all movements, even simple standing and short duration walking would increase these patients' autonomy and quality of life. The stimulating array technology described herein (e.g., epidural stimulating arrays) paves the way for a direct brain-to-spinal cord interface that could enable more lengthy and finer control of movements.

While the methods and devices described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, and the like).

In various embodiments, the methods combine the use of epidural stimulating arrays with physical training (e.g., rigorously monitored (robotic) physical training), optionally in combination with pharmacological techniques. The methods enable the spinal cord circuitry to utilize sensory input as well as newly established functional connections from the brain to circuits below the spinal lesion as a source of control signals. The approach is thus designed to enable and facilitate the natural sensory input as well as supraspinal connections to the spinal cord in order to control movements, rather than induce the spinal cord to directly induce the movement. That is, we facilitate and enhance the intrinsic neural control mechanisms of the spinal cord that exist post-SCI, rather than replace or ignore them.

Processing of Sensory Input by the Lumbosacral Spinal Cord: Using Afferents as a Source of Control In various embodiments the methods and devices described herein exploit spinal control of locomotor activity. For example, the human spinal cord can receive sensory input associated with a movement such as stepping, and this sensory information can be used to modulate the motor output to accommodate the appropriate speed of stepping and level of load that is imposed on lower limbs. Moreover, we have demonstrated that the human lumbosacral spinal cord has central-pattern-generation-like properties. Thus, oscillations of the lower limbs can be induced simply by vibrating the vastus lateralis muscle of the lower limb, by epidural stimulation, and by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like. The methods described herein facilitate and adapt the operation of the existing spinal circuitry that generates, for example, cyclic step-like movements via a combined approach of epidural stimulation, physical training, and, optionally, pharmacology.

Facilitating Stepping and Standing in Humans Following a Clinically Complete Lesion Locomotion in mammals is attributed to intrinsic oscillating spinal neural networks capable of central pattern generation interacting with sensory information (Edgerton et al., *J. American Paraplegia Soc,* 14(4) (1991), 150-157; Forssberg, *J. Neurophysiol,* 42(4): 936-953 (1979); Grillner and Wallen, *Annu. Rev. Neurosci.,* 8: 233-261 (1985); Grillner and Zangger, *Exp Brain Res,* 34(2): 241-261 (1979)). These networks play critical roles in generating the timing of the complex postural and rhythmic motor patterns executed by motor neurons.

As indicated above, the methods described herein can involve stimulation of one or more regions of the spinal cord in combination with locomotory activities. It was our discovery that spinal stimulation in combination with locomotor activity results in the modulation of the electrophysiological properties of spinal circuits in the subject so they are activated by proprioceptive information derived from the region of the subject where locomotor activity is to be facilitated. Further, we also determined that spinal stimulation in combination with pharmacological agents and locomotor activity results in the modulation of the electrophysiological properties of spinal circuits in the subject so they are activated by proprioceptive information derived from the region of the subject where locomotor activity is to be facilitated.

Locomotor activity of the region of interest can be accomplished by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs are loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Epidural Stimulation of the Lumbosacral Spinal Cord

As indicated above, without being bound by a particular theory, it is believed that epidural stimulation, e.g., over the lumbosacral spinal cord in combination with physical training can facilitate recovery of stepping and standing in human subjects following a complete SCI.

Spinal cord electrical stimulation has been successfully used in humans for suppression of pain and spasticity (see, e.g., Johnson and Burchiel, *Neurosurgery,* 55(1): 135-141

(2004); discussion 141-142; Shealy et al., *Anesth Analg*, 46(4): 489-491 (1967); Campos et al., *Appl. Neurophysiol.* 50(1-6): 453-454 (1987); Dimitrijevic and Sherwood, *Neurology*, 30 (7 Pt 2): 19-27 (1980); Barolat *Arch. Med. Res.*, 31(3): 258-262 (2000); Barolat, *J. Am. Paraplegia Soc.*, 11(1): 9-13 (1988); Richardson et al., *Neurosurgery*, 5(3): 344-348). Recent efforts to optimize electrode design and stimulation parameters have led to a number of research studies focusing on the benefits of epidural spinal cord stimulation. We have demonstrated that the location of the electrode array and its stimulation parameters are important in defining the motor response. Use of high density electrode arrays, as described herein, facilitates selection or alteration of particular stimulation sites as well as the application of a wide variety of stimulation parameters.

Figure 1:
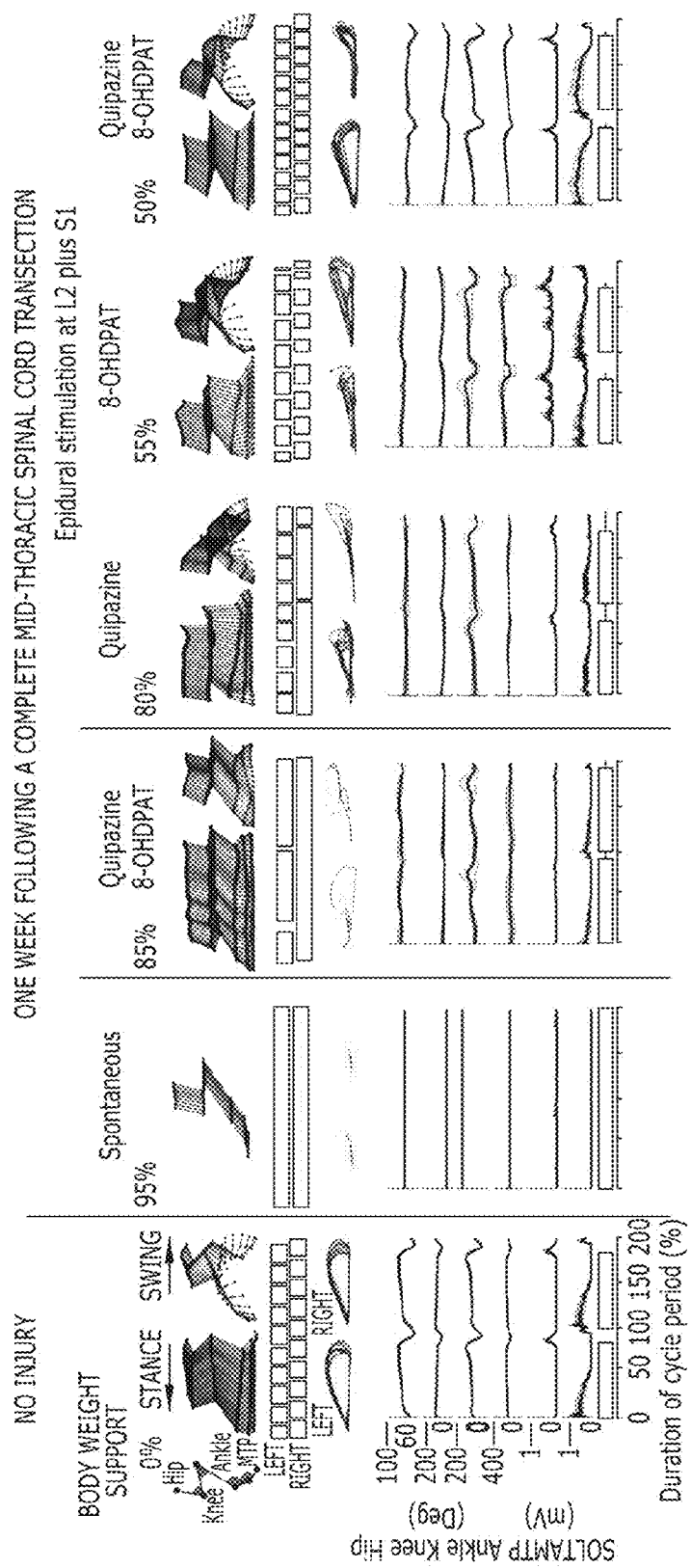

FIG. 1 summarizes experiments in rats that were carried out to assess the effectiveness of epidural stimulation coupled with combined drug therapy in acute treatment of complete spinal cord injury. These experiments also show that pharmacological intervention provides some recovery of stepping function, but that epidural stimulation coupled with drug therapy recovers significant amounts of stepping ability even one week after a complete spinal transaction.

Figure 2:
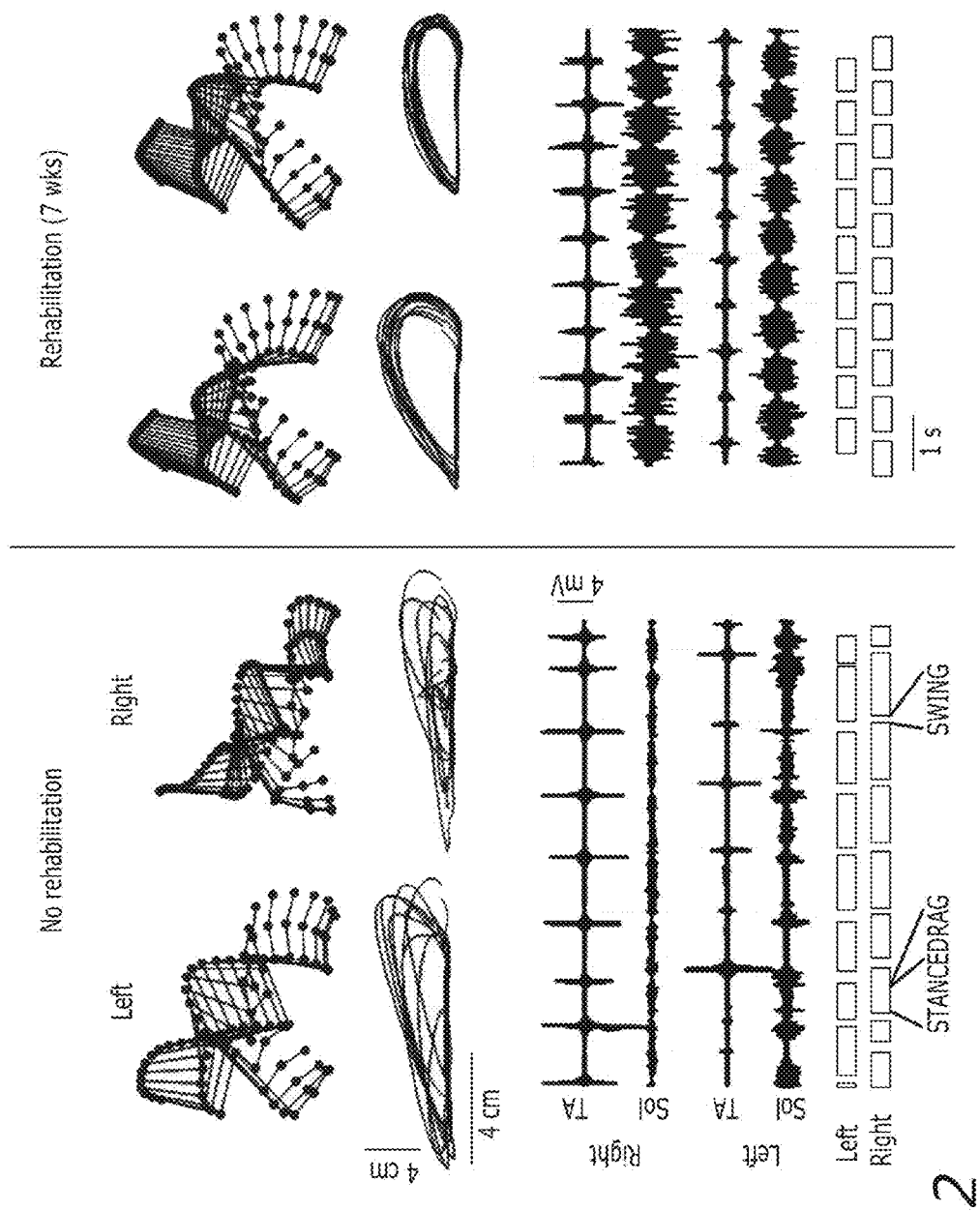
Figure 5A:
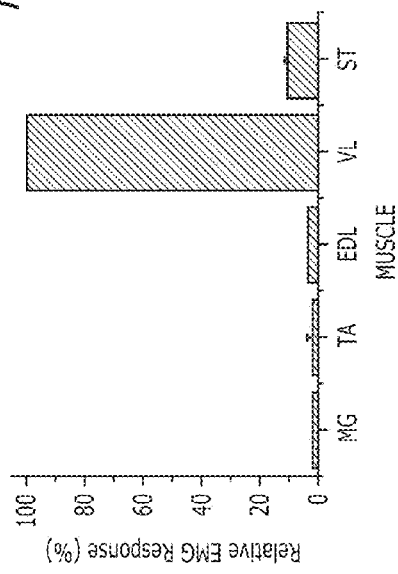
Figure 5C:
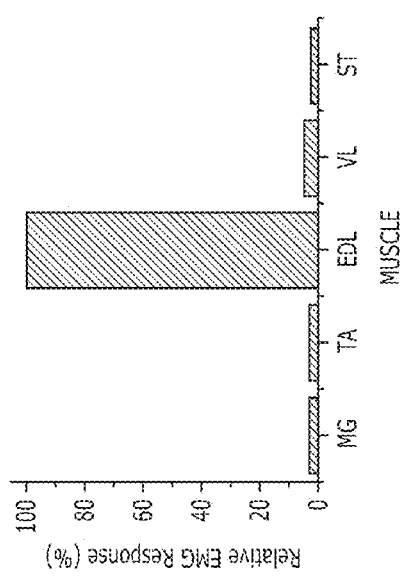
Figure 5B:
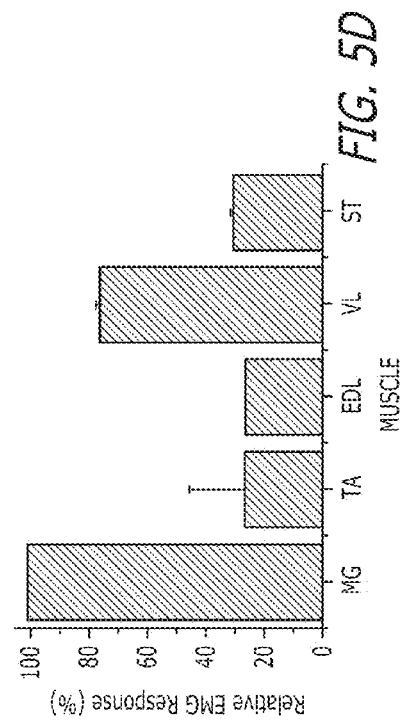
Figure 5D:
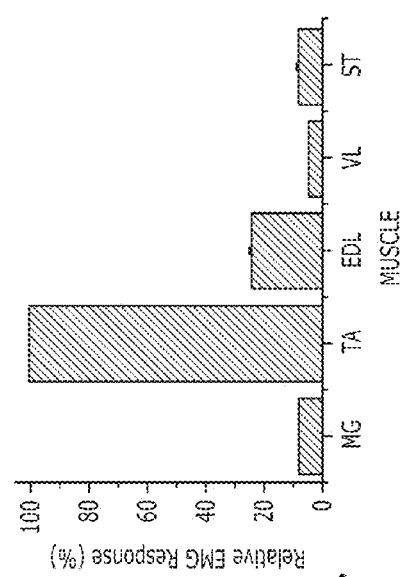

FIG. 2 compares two adult rats with complete spinal cord transections at the end of a 7 week period during which both animals were given both drug therapy as well as epidural stimulation (using conventional rod-electrodes at two spinal sites). The animal which was also given robotically guided physical therapy showed significant improvement over the animal which did not receive physical training. These results provide support for our assertion that a strategy that combines physical therapy with epidural stimulation and, optional, pharmacological modulation of the post-SCI spinal circuits can facilitate standing and stepping recovery in humans.

MicroFabricated High-Density Epidural Stimulating Arrays

In various embodiments, the epidural electrical stimulation is administered via a high density epidural stimulating array. In certain embodiments, the high density electrode arrays use microfabrication technology to place numerous electrodes in an array configuration on a flexible substrate. One suitable epidural array fabrication method was first developed for retinal stimulating arrays (see, e.g., Maynard, *Annu. Rev. Biomed. Eng.*, 3: 145-168 (2001); Weiland and Humayun, *IEEE Eng. Med. Biol. Mag.*, 24(5): 14-21 (2005)), and U.S. Patent Publications 2006/0003090 and 2007/0142878 which are incorporated herein by reference for all purposes (e.g., the devices and fabrication methods disclosed therein). In various embodiments the stimulating arrays comprise one or more biocompatible metals (e.g., gold, platinum, chromium, titanium, iridium, tungsten, and/or oxides and/or alloys thereof) disposed on a flexible material (e.g., parylene A, parylene C, parylene AM, parylene F, parylene N, parylene D, or other flexible substrate materials). Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, *Medical Device and Diagnostic Industry*, 22(8): 42-49 (2000)), and has flexibility characteristics (Young's modulus ~4 GPa (Rodger and Tai, *IEEE Eng. Med. Biology*, 24(5): 52-57 (2005))), lying in between those of PDMS (often considered too flexible) and most polyimides (often considered too stiff). Finally, the tear resistance and elongation at break of parylene are both large, minimizing damage to electrode arrays under surgical manipulation (Rodger et al., *Sensors and Actuators B-Chemical*, 117(1): 107-114 (2006)).

The electrode array may be implanted using any of a number of methods (e.g., a laminectomy procedure) well known to those of skill in the art.

FIG. 3 shows a first prototype microelectrode array, scaled for mice, in which ten 250 micron diameter platinum electrodes are microfabricated onto a 2 mm wide Parylene backing. The electrodes are dorsally implanted using a laminectomy over the lumbosacral spinal cord, with one electrode placed over each intravertebral segment. In chronic implantation studies (using rat, mice, and pig animal models) of up to 6 months, we have shown high biocompatibility of these arrays with mammalian tissue. Implantation of an array into a human subject is described in Example 1.

Of course, other microarray embodiments are contemplated. In certain embodiments, the number of electrodes formed on an electrode array can vary from one electrode to about 100,000 electrodes or more. In certain embodiments, the electrode microarray comprises at least 10, at least 15, at least 20, at least 25, at least 50, at least 100, at least 250, at least 500, or at least 1000 electrodes. In various embodiments the interelectrode spacing of adjacent electrodes in the electrode array varies from about 100 µm or about 500 µm, or about 1000 µm or about 1500 µm to about 2000 µm, or about 3000 µm, or about 4000 µm, or about 4500 µm, or about 5000 µm. In various embodiments, interelectrode spaking ranges from about 100 µm, about 150 µm, about 200 µm, or about 250 µm up to about 1,000 µm, about 2000 µm, about 3000 µm, or about 4,000 µm. In various illustrative embodiments, individual electrode diameters (or width) range from about 50 µm, 100 µm, 150 µm, 200 µm, or 250 µm up to about 500 µm, about 1000 µm, about 1500 µm, or about 2000 µm.

The electrode array can be formed in any geometric shape such as a square or circular shape; typically the size of the array will be on the order of about 0.1 mm to about 2 cm, square or in diameter, depending in part on the number of electrodes in the array. In various embodiments, the length of an electrode array ranges from about 0.01 mm, or 0.1 mm up to about 10 cm or greater.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

FIG. 16 shows EMG responses from different muscle groups to different types of stimulation (monopolor and bipolar) at different spinal sites. These data show that our strategy of spatially selective epidural stimulation of different portions of the lumbosacral spinal cord can focally excite and coordinate the muscle groups that are involved in locomotion.

We have also developed and tested in rats more complex twenty-seven electrode arrays, which are arranged in a 9×3 pattern so that there are 3 electrodes (mid-line, left, and right) at each of 9 intravertebral segments (FIG. 7). These arrays have been tested for up to 6 weeks in vivo, showing biocompatibility as well as stepping capability that betters the previous results we have obtained with conventional electrodes. FIG. 8 shows a 256 electrode array that was fabricated to demonstrate the potential for multi-layer fabrication technology to build an array of hundreds of electrodes.

Embodiments of the electrode arrays described herein may be constructed to offer numerous advantages. For example, flexible parylene electrode arrays are mechanically stable. Their flexibility allows them to conform to the contours of the spinal cord, forming a thin layer (e.g., 10 µm thick) that adheres to the cord. This close fit facilitates connective tissue encapsulation, which also enhances fixation.

The arrays may also offer spatially selective stimulation. Early studies of stimulation protocols to facilitate locomotion in SCI animals delivered stimuli to a single spinal cord region as the ideal stimulation site was hypothesized to be fixed and species-specific. Researchers identified "optimal" stimulation sites for cats (Gerasimenko et al., *Neurosci. Behav. Physiol.*, 33(3): 247-254 (2003)) and for rats (Gerasimenko et al., *J Neurosci. Meth.*, 157(2): 253-263 (2006)) at a single time point after injury. However, the optimal stimulation site may not be constant. Rat studies showed that while stimulation at the L2 spinal level facilitated the best stepping soon after a complete transection, S1 stimulation produced more effective stepping several weeks later (Id.). Similarly, clinical data from patients receiving SCS for the treatment of lower back pain indicates that continued pain suppression often requires adjustment of the electrode position (Carter, *Anaesth. Intensive Care*, 32(1): 11-21 (2004)). These data support the hypothesis that the optimal stimulation pattern is not fixed. After a traumatic injury, the spinal cord is continuously modified by the progression of secondary damage, as well as the post-injury therapies. Our arrays' high electrode density enables ongoing identification of the optimal stimulation patterns. Our arrays' high-density allows adjustment of the stimulating pattern to account for migration, or for initial surgical misalignment.

The electrode arrays described herein also facilitate the use of advanced stimulation paradigms. Given the complex chain of reflexes involved, for example, in stepping, we believe that more sophisticated spatiotemporal stimulation patterns, involving either simultaneous or sequential stimulation of different spinal cord regions, may facilitate improved posture and locomotion and reaching and grasping compared with simple patterns. The high electrode densities allow us to test advanced stimulation paradigms that have previously been infeasible to study.

In addition, the electrode arrays provide for a lower charge injection amplitude and lower power consumption. The close positioning to the spinal cord possible with electrode arrays described herein minimizes the required levels of charge injection and power consumption. Since long-term tissue damage caused by electrical stimulation is proportional to injected charge, our conformal arrays allow longer sustained bouts of stimulation. This is desirable for long-term stimulation therapy and for battery-powered implants.

The electrode arrays described herein facilitate the measurement and evaluation of evoked potentials. Our electrode arrays can record field potentials from the dorsum (or other regions) of the spinal cord. Spinal somatosensory evoked potentials (SSEPs) measured from different levels of the spinal cord can be used to assess the state of the spinal cord and, potentially, to identify and classify the nature of a spinal injury. SSEPs are typically composed of a series of responses. With an array, response latency, amplitude, and conduction velocity can be simultaneously gathered from positions throughout the lumbosacral spinal cord. Examining the SSEPs for different injury types facilitates the generation of an injury-specific atlas of spinal potentials. SSEPs can be used as a measure of recovery and to evaluate the potential effectiveness of different treatment paradigms that might be applied. Monitoring SSEPs at different time points after the start of a treatment provides insight into the synaptic mechanisms that are involved in reacquiring locomotor function, and also serve as a diagnostic of how and if a particular strategy is aiding recovery. For example, recent data collected in our lab suggests that the return of polysynaptic spinal responses may be correlated with regaining the ability to step.

Use of Machine Learning to Select Optimal Electrode Array Stimulation Parameters High density epidural stimulating electrode arrays can provide patient-customized stimuli, compensate for errors in surgical placement of the array, and adapt the stimuli over time to spinal plasticity (changes in spinal cord function and connectivity). However, with this flexibility comes the burden of finding suitable stimuli parameters (e.g., the pattern of electrode array stimulating voltage amplitudes, stimulating currents, stimulating frequencies, and stimulating waveform shapes) within the vast space of possible electrode array operating patterns. It is not practical to exhaustively test all possible parameters within this huge space to find optimal parameter combinations. Such a process would consume a large amount of clinical resources. A machine learning algorithm can employed to more efficiently search for effective parameter combinations. Over time, a machine learning algorithm can also be used to continually, occasionally, and/or periodically adapt the stimulation operating parameters as needed.

A machine learning algorithm that seeks to optimize the stimuli parameters desirably alternates between exploration (searching the parameter space and building a regression model that relates stimulus and motor response) and exploitation (optimizing the stimuli patterns based on the current regression model). Many machine learning algorithms incorporate exploration and exploitation phases, and any learning algorithm that incorporates these two phases can be employed as a procedure to select (e.g., optimize) the electrode array stimulating parameters over time.

One particular embodiment relies upon Gaussian Process Optimization (GPO) (Rasmussen, *Gaussian Processes for Machine Learning*, MIT Press (2006)), an active learning method whose update rule explores and exploits the space of possible stimulus parameters while constructing an online regression model of the underlying mapping from stimuli to motor performance (e.g., stepping, standing, or arm reaching). Gaussian Process Regression (GPR), the regression modeling technique at the core of GPO, is well suited to online use because it requires fairly minimal computation to incorporate each new data point, rather than the extensive recomputation of many other machine learning regression of models lying within a restricted set, rather than from a single model, allowing it to avoid the over-fitting difficulties inherent in many parametric regression and machine learning methods.

GPR is formulated around a kernel function, k(,), that can incorporate prior knowledge about the local shape of the performance function (obtained from experience and data derived in previous epidural stimulation studies), to extend inference from previously explored stimulus patterns to new untested stimuli. Given a function that measures performance (e.g., stepping, standing, or reaching), GPO is based on two key formulae and the selection of an appropriate kernel function. The core GPO equation describes the predicted mean $\mu_t(x^*)$ and $\sigma_t^2(x^*)$ of the performance function (over the space of possible stimuli), at candidate stimuli $x^*$, on the basis of past measurements (tests of stimuli values $X=\{x_1, x_2, \ldots\}$ which returned noisy performance values $Y_t=\{y_1, y_2, \ldots\}$)

$$\mu_t(x^*)=k(x^*,X)[K_t(X,X)+\sigma_n^2 I]^{-1} Y_t;$$

$$\sigma_t^2(x^*)=k(x^*,x^*)-k(x^*,X)[K_t(X,X)+\sigma_n^2 I]^{-1} k(X,x^*)$$

where $K_t$ is the noiseless covariance matrix of past data, and $\sigma_n^2$ is the estimated noise covariance of the data that is used in the performance evaluation. To balance exploration of regions of the stimuli space where little is known about expected performance with exploitation of regions where we expect good performance, GPO uses an upper confidence bound update rule (Srinivas and Krause, *Gaussian Process Optimization in the bandit setting: No Regret and Experimental Design*, Proc. Conf. on Machine Learning, Haifa Israel (2010)).

$$x_{i+1}=\operatorname{argmax}_{xnX*}[\mu_t(x)+\beta_t\sigma_t(x)].$$

When the parameter $\beta_t$ increase with time, and if the performance function is a Gaussian process or has a low Reproducing Kernel Hilbert Space norm relative to a Gaussian process, GPO converges with high probability to the optimal action, given sufficient time.

The definition of a performance function that characterizes human motor behavior (e.g. standing or stepping behavior) typically depends upon two factors: (1) what kinds of motor performance data is available (e.g., video-based motion capture data, foot pressure distributions, accelerometers, electromyographic (EMG) measurements, etc.); and (2) the ability to quantify motor performance. While more sensory data is preferable, a machine learning approach to parameter optimization can employ various types of sensory data related to motor performance. It should be noted that even experts have great difficulty determining stepping or standing quality from such data without also looking at video or the actual subject as they undertake a motor task. However, given a sufficient number of training examples from past experiments and human grading of the standing or stepping in those experiments, a set of features that characterize performance (with respect to the given set of available sensors) can be learned and then used to construct a reasonable performance model that captures expert knowledge and that uses the available measurement data.

FIGS. 18A-18B depict a multi-compartment physical model of the electrical properties of mammalian spinal cord, along with a 27 electrode array placed in an epidural position. FIGS. 18A-18B also show the isopotential contours of the stimulating electric field for the 2-electrode stimulation example. FIG. 19 shows the instantaneous and average "regret" (a measure of the error in the learning algorithms search for optimal stimuli parameters) when the Gaussian Process Optimization algorithm summarized above is used to optimize the array stimulus pattern that excites neurons in the dorsal roots between segments L2 and S2 in the simulated spinal cord. The instantaneous regret performance shows that the learning algorithm rapidly finds better stimulating parameters, but also continually explores the stimulation space (the "bursts" in the graph of instantaneous regret correspond to excursions of the learning algorithm to regions of stimulus parameter space which were previously unknown, but which have been found to have poor performance).

Use of Robotically Guided Training to Assist Recovery of Standing and Stepping

FIG. 2 shows that the use of physical training in combination with epidural stimulation and drug therapy produces better stepping behavior. Similarly, Example 1, herein, shows a similar effect of the combination of epidural stimulation and physical training/loading in a human subject.

While such physical manipulation can be facilitated by the use of trainers, e.g., as described above and in Example 1, in certain embodiments, the use of robotic devices and novel robotic control algorithms to guide and monitor the physical training process is contemplated. Robotic devices have been used successfully to train stepping and standing in complete spinal cord injured laboratory animals (Fong et al., *J Neuroscience*, 25(50): 11738-11747 (2005); de Leon et al., *Brain Res Brain Res Rev.*, 40(1-3): 267-273 (2002); de Leon et al., *J Neurophysiol.*, 182(1): 359-369 (1999)). However, recovery of effective patterns and levels of neuromuscular activity in humans with SCI (without epidural stimulation) as a result of training with a robotic device has not yet been as successful (Wernig, *Arch Phys Med Rehabil.*, 86(12): 2385-2386 (2005); author reply 2386-2387).

It is contemplated that "assist-as-needed" control algorithms that mimic the behavior of human therapists during weight supported treadmill step training of human SCI patients can be utilized. When the limb kinematics of the SCI patient are poor, the therapists provides a large amount of physical bias to force the limbs to follow a more normal stepping pattern, as well as cutaneous sensory input to trigger reflex responses. When the limbs are moving close to a normal stepping pattern, the therapist provides little physical bias or sensory input to the patient. We implemented these algorithms on the robot of FIG. 9, and found that even primitive assist-as-needed algorithms provide significant improvement in the rate and quality of step recovery. In this robotic device, lightweight low-friction robot arms guide the motions of the ankles of a weight-supported spinalized animal (mouse or rat) as it steps at various speeds on the moving treadmill. Because of the arms' low mass, they can also be used in a passive mode for testing locomotion ability—the movements of the animal's ankles are recorded by the robot as it attempts to walk on the treadmill (see, e.g., Cai, et al., *Proc. Int. Conference Rehab. Robotics.*, 9: 575-579 (2005)).

Pharmacological Facilitation of Stepping, Standing, Reaching and Grasping

In certain embodiments, the methods described herein are used in conjunction with various pharmacological agents. In particular, the use of various serotonergic, and/or dopaminergic, and/or noradrenergic and/or GABAergic, and/or glycinergic drugs, particularly drugs that have been demonstrated to be effective in facilitating stepping in animals is contemplated. These agents can be used in combination with epidural stimulation and physical therapy as described above. This combined approach can help to put the spinal cord (below the site of lesion) in an optimal physiological state for controlling a range of lower and upper limb movements.

In certain embodiments, the drugs are administered systemically, while in other embodiments, the drugs are administered locally, e.g., to particular regions of the spinal cord. Drugs that modulate the excitability of the spinal neuromotor networks are combinations of noradrenergic, serotonergic, GABAergic, and glycinergic receptor agonists and antagonists. Illustrative pharmacological agents include, but are not limited to agonists and antagonists to one or more combinations of serotonergic: 5-HT1A, 5-HT2A, 5-HT3, and 5HT7 receptors; to noradrenergic alpha1 and 2 receptors; and to dopaminergic D1 and D2 receptors (see, e.g., Table 1).

TABLE 1

Illustrative pharmacological agents.

| Name | Target | Action | Route | Optimal Concentration (mg/Kg) | Range of tested concentrations (mg/Kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| QUIPAZINE | 5-HT2A/C | Agonist | I.P. | 0.2 | 0.18-0.6 |
| KETANSERIN | 5-HT2A/C | Antagonist | I.P. | 3 | 1.5-6.0 |
| SR 57227A | 5-HT3 | Agonist | I.P. | 1.5 | 1.3-1.7 |
| ONDANSETRON | 5-HT3 | Antagonist | I.P. | 3 | 1.4-7.0 |
| SB 269970 | 5-HT7 | Antagonist | I.P. | 7 | 2.0-10.0 |
| Noradrenergic receptor systems | | | | | |
| METHOXAMINE | Alpha1 | Agonist | I.P. | 2.5 | 1.5-4.5 |
| PRAZOSIN | Alpha1 | Antagonist | I.P. | 3 | 1.8-3.0 |
| CLONIDINE | Alpha2 | Agonist | I.P. | 0.5 | 0.2-1.5 |
| YOHIMBINE | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| QUINPIROLE | D2-like | Agonist | I.P. | 0.3 | 0.15-0.3 |
| ETICLOPRIDE | D2-like | Antagonist | I.P. | 1.8 | 0.9-1.8 |

The foregoing embodiments are intended to be illustrative and not limiting. Using the teachings and examples provided herein, numerous variations on the methods and devices described herein will be available to one of ordinary skill in the art.

EXAMPLES

The following examples are offered to illustrate, but not to limit the claimed invention.

Example 1

Epidural Stimulation of the Lumbosacral Spinal Cord Enables Independent Standing, Voluntary Movement, and Assisted Stepping in a Paraplegic Human This example demonstrates that the human spinal cord circuitry has the ability to generate postural and locomotor patterns without supraspinal motor input. This capability and voluntary movement can be manifested when the excitability of these networks is modulated by epidural stimulation at a level that enables proprioceptive input to provide a source of neural control to elicit the motor pattern appropriate for the task.

Introduction

The mammalian spinal cord can generate locomotor output in the absence of input from the brain. See Grillner S., Neurobiological bases of rhythmic motor acts in vertebrates, Science, 228:143-149 (1985); and Rossignol S, Barriere G, Frigon A, Barthelemy D, Bouyer L, Provencher J, et al., Plasticity of locomotor sensorimotor interactions after peripheral and/or spinal lesions, Brain Res Rev, 57(1):228-240 (January 2008). This capability has been attributed to the phenomenon of central pattern generation. See Grillner S, Wallen Peter, Central pattern generators for locomotion, with special reference to vertebrates, Ann Rev Neurosci, 8:233-261 (1985); and Grillner S, Zangger P., On the central generation of locomotion in the low spinal cat, Exp Brain Res, 34:241-261 (1979). Functional standing and stepping can be executed by cats with complete transection of the spinal cord when sensory input is provided to the lumbosacral locomotor pattern generator circuitry. See de Leon R D, Hodgson J A, Roy R R, Edgerton V R., Locomotor capacity attributable to step training versus spontaneous recovery after spinalization in adult cats, J Neurophysiol, 79:1329-1340 (1998); and Barbeau H, and Rossignol S., Recovery of locomotion after chronic spinalization in the adult cat, Brain Res, 412:84-95 (1987). Spinal cats can learn to stand, fully supporting their hindquarters, and to step over a range of speeds and load-bearing levels with task specific training. Adult spinally transected rats, unlike cats, can generate stepping only with additional combined interventions of locomotor training, pharmacological intervention, and/or epidural stimulation. See Courtine G, Gerasimenko Y, van den BR, Yew A, Musienko P, Zhong H, et al., Transformation of nonfunctional spinal circuits into functional states after the loss of brain input, Nat Neurosci, 12(10):1333-1342 (October 2009); and Ichiyama R M, Courtine G, Gerasimenko Y P, Yang G J, van den B R, Lavrov I A, et al., Step training reinforces specific spinal locomotor circuitry in adult spinal rats, J Neurosci, 16; 28(29):7370-7375 (July 2008). These observations demonstrate a level of automaticity sufficient to generate locomotion without any supraspinal influence. This evidence leads to the hypothesis that if similar spinal circuits exist in humans then electrically stimulating the lumbosacral spinal cord epidurally should be able to facilitate standing and stepping in an individual with a motor complete spinal cord injury.

Although, rhythmic motor patterns of the legs have been observed, 12-15 sustained independent, full weight-bearing standing and stepping has not been reported in humans after complete motor paralysis. See Calancie B., Spinal myoclonus after spinal cord injury, J Spinal Cord Med, 29:413-424 (2006); Dimitrijevic M R, Gerasimenko Y, Pinter M M, Evidence for a spinal central pattern generator in humans, Ann NY Acad Sci, 16; 860:360-376 (November 1998); Kuhn R A. Functional capacity of the isolated human spinal cord, Brain, 73(1):1-51 (1950); and Nadeau S, Jacquemin G, Fournier C, Lamarre Y, Rossignol S., Spontaneous motor rhythms of the back and legs in a patient with a complete spinal cord transection, Neurorehabil Neural Repair, 24(4): 377-383 (May 2010). However, after a motor incomplete SCI functional improvements occur with intense locomotor training and with epidural stimulation. See Wernig A, and Muller S., Laufband locomotion with body weight support improved walking in persons with severe spinal cord injuries, Para; 30:229-238 (1992); Wemig A, Nanassy A, Muller S., Maintenance of locomotor abilities following Laufband (treadmill) therapy in para- and tetraplegic persons: follow-up studies, *Spinal Cord,* 36:744-749 (1998); and Herman R, He J, D'Luzansky S, Willis W, Dilli S., Spinal cord stimulation facilitates functional walking in a chronic, incomplete spinal cord injured. Spinal Cord, 40(2):65-68 (February 2002). Rhythmic efferent activity timed to the step cycle, however, can occur during manually facilitated stepping and bilateral tonic activity can occur during partial weight bearing standing in individuals with a clinically complete SCI after extensive task specific training. See Dietz V, Colombo G, Jensen L., Locomotor activity in spinal man, *The Lancet,* 344:1260-1263 (1994); Harkema S J, Hurley S L, Patel U K, Requejo P S, Dobkin B H, Edgerton V R, Human lumbosacral spinal cord interprets loading during stepping, *J Neurophysiol,* 77(2):797-811 (1997); and Harkema S J, Plasticity of interneuronal networks of the functionally isolated human spinal cord, *Brain Res Rev,* 57(1):255-264 (January 2008). Rhythmic and tonic motor patterns of the legs have been induced via epidural stimulation in humans after motor complete SCI while lying supine. See Dimitrijevic M R, Gerasimenko Y, Pinter M M, Evidence for a spinal central pattern generator in humans, *Ann NY Acad Sci,* 16; 860:360-376 (November 1998); Gerasimenko Y, Daniel 0, Regnaux J, Combeaud M, Bussel B., *Mechanisms of locomotor activity generation under epidural spinal cord stimulation,* In: Dengler R, Kossev A, editors, Washington, D.C.: IOS Press, p. 164-171 (2001); and Minassian K, Jilge B, Rattay F, Pinter M M, Binder H, Gerstenbrand F, et al., Stepping-like movements in humans with complete spinal cord injury induced by epidural stimulation of the lumbar cord: electromyographic study of compound muscle action potentials, *Spinal Cord,* 42(7):401-416 (July 2004). This suggests that spinal circuitry for locomotion is present in the human but cannot functionally execute these tasks without some level of excitability from supraspinal centers that may be present after incomplete SCI.

We hypothesized that tonic epidural spinal cord stimulation can modulate the human spinal circuitry into a physiological state that enables sensory input derived from standing and stepping movements to serve as a source of neural control to perform these tasks. We observed that the spinal circuitry was able to generate independent standing in response to task specific sensory cues in the presence of epidural stimulation in a paraplegic subject with a motor complete spinal cord injury. Stepping-like patterns were also generated with epidural stimulation with the subject on a treadmill using body weight support and manual facilitation. The subject also regained some voluntary control of the legs seven months post implantation. We have used epidural stimulation to substitute for descending signals that normally come from the brain to modulate the physiological state of the spinal networks and the sensory information can be used as a source of neural control of the motor task. Unexpectedly, clinical assessments indicated improvements in other physiological functions including bladder, sexual function and temperature regulation.

Methods

Clinical Characteristics Prior to Implantation.

The subject is a 23 year old man who had been struck by a motor vehicle 3.4 years prior to implantation. He sustained a C7-T1 subluxation with injury to the lower cervical and upper thoracic spinal cord. Neurological examination revealed paraplegia. The triceps and intrinsic hand muscles exhibited voluntary contraction but were weak. He had no contraction of trunk or leg muscles. He was treated emergently with reduction of the subluxation by anterior interbody fusion and instrumentation. Magnetic resonance imaging of the injury site obtained prior to implantation revealed myelomalacia and atrophy of the cord segment adjacent to the T1 vertebral body (see FIG. 10A).

Prior to the lumbosacral epidural implantation his neurological deficit was classified using the American Spinal Injury Association (ASIA) impairment scale (AIS) as ASIA B (pinprick and light-touch present below the lesion). Marino R J, Barros T, Biering-Sorensen F, Burns S P, Donovan W H, Graves D E, et al., International standards for neurological classification of spinal cord injury, *J Spinal Cord Med,* 26 Suppl 1:S50-S56 (2003). He had no motor function of trunk or leg muscles, a flaccid anal sphincter, and no voluntary bladder contraction (see FIG. 10B). Sensation was abnormal below C7.

Somatosensory evoked potentials showed bilateral delay of cortical responses from posterior tibial nerve stimulation. Latencies of sensory evoked potentials recorded at Erb's point, cervical, and contralateral cortical sites in response to median nerve stimulation at the wrist were within normal ranges. Lower extremity nerve conduction studies were normal. No response was elicited from leg muscles by transcranial magnetic stimulation of the motor cortex using a butterfly coil centered over Cz. He was unable to stand or walk independently or voluntarily move his legs despite standard-of-care rehabilitation and additional intensive locomotor training.

The research subject signed an informed consent for electrode implantation, stimulation, and physiological monitoring studies that was approved by the University of Louisville and the University of California, Los Angeles Institutional Review Boards. To be certain there was no remaining potential for standing and walking, prior to the electrode implantation, the participant received 170 locomotor training sessions over a period of 26 months using body weight support on a treadmill with manual facilitation resulting in 108 hours of step training and 54 hours of stand training with no detectable change in EMG activity (see FIG. 12). During standing, throughout training no observable EMG was evident. During assisted stepping, sporadic EMG activity was observed in the lower leg muscles, most often in the medial hamstrings, however, was never observed EMG activity in all muscles bilaterally. No detectable improvement in EMG was noted over the course of the training.

Surgical Implantation of Electrode Array and Stimulator

An epidural spinal cord stimulation unit (Medtronics, Restore Advanced) was used to electrically stimulate the lumbar-sacral enlargement. A 16-electrode array was implanted epidurally under fluoroscopic control at T11-L1 over lumbosacral spinal cord segments L1-S1 (see FIG. 11A). The location of the electrode array was evaluated and adjusted during surgery with fluoroscopy and electrophysiologically with EMG recorded from leg muscles. See Murg M, Binder H, Dimitrijevic M R, Epidural electric stimulation of posterior structures of the human lumbar spinal cord: 1. muscle twitches—a functional method to define the site of stimulation, *Spinal Cord,* 38:394-402 (2000). EMG responses were elicited by epidural stimulation at 2 Hz during a sequence of increasing voltages and specific electrode configurations to determine threshold of muscle activation and amplitude of the response. A midline stimulation configuration was followed using one cathode and one anode electrode, with each electrode pair being 6 mm apart.

Multiple stimulation combinations were performed ranging from most rostral to most caudal positions. Symmetry was also tested by using left and right side electrodes within the array. The electrode lead was tunneled to a subcutaneous abdominal pouch where the pulse generator was implanted. Two weeks after implantation the position of the array was reconfirmed with the subject lying supine using the same stimulation protocols (see FIGS. 11C-11D).

Experimental Design

Stimulation parameters were systematically evaluated to identify the optimal stimulation parameters for generating efferent patterns for standing and stepping. Stimulation of the spinal cord was carried out during sessions lasting up to 250 minutes in which physiological parameters were measured. The total duration of stimulation during each experimental session ranged from 40 minutes to 120 minutes. Stimulation amplitudes ranged from 0.5 V to 10.0 V and stimulation frequencies from 5 to 40 Hz using either a 210 or 450 μs pulse width. The optimal configurations for standing were those with which sustainable tonic co-activation were evoked; for stepping optimal configurations were those in which rhythmic activity was present with alternation of right and left leg and intralimb flexors and extensors. EMG activity of 14 lower extremity muscles and hip, knee, and ankle joint angles were measured.

During experimental sessions on the treadmill, level of body weight support (Innoventor, St. Louis, Mo.) and amount of body weight load were also measured. Trainers provided manual facilitation, when needed, distal to the patella during the stance phase, and at the popliteal fossa and anterior distal tibia for foot clearance during the swing phase and at the pelvis for stabilization and weight shifting during stepping. Stand training was performed using a custom-made standing device designed to provide full weight-bearing and pelvis support. The device included vertical and horizontal bars positioned about (or surrounding) the subject to allow him to assist balance. Bungees were attached to the device to provide support only if the knees or hips flexed beyond the normal standing posture. The total duration of stimulation during each session averaged 44 minutes (sessions 1-34) and 60 minutes (sessions 35-80). Epidural stimulation was not provided outside laboratory sessions. The subject attempted to stand for 60 minutes during each training session. To optimize independent standing stimulation parameters (electrode configuration, voltage and frequency) were modified approximately once per week.

During sitting, stimulation voltage was increased to a desired level. This voltage was kept constant as the subject went from sitting to standing and throughout the standing bout. The subject initiated the sit to stand transition by positioning his feet shoulder width apart and shifting his weight forward to begin loading the legs. The subject used the bars of the standing device during the transition phase to balance and to partially pull himself into a standing position. Trainers positioned at the pelvis and knees assisted as needed during the sit to stand transition. Elastic bungees posterior to the pelvis were set by one of the trainers after the subject achieved full-weight bearing standing. These bungees helped the subject sustain appropriate pelvic tilt and position and allowed him to safely stand with minimal assistance.

During the standing bout, one trainer assisted the subject by applying posteriorly directed gentle pressure at the patellar tendon as necessary to maintain knee extension. The subject was encouraged to stand for as long as possible throughout the session.

Seated resting periods occurred when requested by the subject and reduced in frequency and duration as the training progressed. No stimulation was provided during the rest periods.

During the first stand session, the subject required 7 breaks (stand time: 60 min; rest time 67 minutes). By session 35, the subject was able to stand for 1 bout lasting a full 60 minutes. The total duration of stimulation averaged across all sessions was 54±13 minutes per session.

Data Acquisition

EMG, joint angles, footswitch, ground reaction forces and BWS data were collected at 2,000 Hz using a 32-channel hard-wired AD board and custom-written acquisition software (National Instruments, Austin, Tex.). Bilateral EMG (Motion Lab Systems, Baton Rouge, La.) from the soleus, medial gastrocnemius, tibialis anterior, medial hamstrings, quadriceps, and gluteus maximus muscles was recorded using bipolar surface electrodes with fixed inter-electrode distance. Harkema S J, Hurley S L, Patel U K, Requejo P S, Dobkin B H, Edgerton V R, Human lumbosacral spinal cord interprets loading during stepping, *J Neurophysiol*, 77(2): 797-811 (1997); and Beres-Jones J A, Johnson T D, Harkema S J, Clonus after human spinal cord injury cannot be attributed solely to recurrent muscle-tendon stretch, *Exp Brain Res*, 149(2):222-236 (March 2003). Bilateral EMG from the iliopsoas was recorded with fine-wire electrodes. Two surface electrodes placed symmetrically lateral to the electrode array incision site over the paraspinal muscles were used to record the stimulation artifact. Hip, knee, and ankle joint angles were acquired using a high speed passive marker motion capture system (Motion Analysis, Santa Rosa, Calif.). Ground reaction forces were collected using shoe-insole pressure sensors FSCAN or HRMAT (TEK-SCAN, Boston, Mass.).

Results

The patient was always aware when the stimulation was on, with the most common sensation being a tingling feeling localized to the thoraco-lumbar electrode implantation site. There was a similar sensation in those muscles that were targeted for activation. Parasthesias were also routinely perceived in the trunk, hips, and legs and varied according to the intensity of stimulation, however were never at a level that produced discomfort or pain and never precluded the use of epidural stimulation.

EMG Activity with Epidural Stimulation for Standing

Epidural stimulation at 15 Hz and 8 V of the caudal segments (L5-S1) of the spinal cord combined with sensory information related to bilateral extension and loading was sufficient to generate standing on day five of stimulation (see FIG. 13). Standing without manual facilitation at the legs was achieved using stimulation (15 Hz, 8 V) with 65% body weight support (see FIG. 13, panel A). The subject was able to sustain standing without any manual facilitation while the level of body weight support was progressively reduced to full weight-bearing (see FIG. 13, panel B).

Transitioning from sitting to standing without body weight support altered the EMG activity during rostral or caudal epidural stimulation even though the parameters remained constant (see FIG. 14). When loading of the legs was initiated, the EMG activity increased dramatically and was sufficient to support the subject's body weight with minimal assistance required by the trainers. During this transition, the stimulation remained constant using the same location, frequency, and intensity parameters (FIG. 14, panels B-E). The EMG activity was also modulated by the site and intensity of stimulation. The EMG activity was dependent on the site and intensity of stimulation with the caudal (L5-S1) stimulation at higher intensities resulting in the most optimal motor pattern for standing (see FIG. 14, panels A-C). During caudal stimulation, there was a more dramatic increase in the EMG amplitude bilaterally in the more proximal muscles while EMG of the more distal muscles was initially markedly reduced (see FIG. 14, panels C and E). Once standing was achieved, there was more co-contraction of both flexors and extensors and proximal and distal muscles with stimulation.

Postural Responses and Independent Standing with Epidural Stimulation

Postural responses were observed in the leg EMG activity when the subject voluntarily shifted his center of gravity sagittally while standing with epidural stimulation and intermittent manual assistance (see FIG. 15, panel A). The EMG burst of the medial gastrocnemius increased with forward deviation, whereas backward deviation induced EMG bursts in the tibialis anterior. Independent standing bouts with tonic bilateral EMG activity routinely occurred for several continuous minutes and increased in frequency and duration as stand training progressed (see FIG. 15, panel B). After 80 sessions, the subject could initiate and maintain continuous independent standing (maximum 4.25 min) with bilateral tonic EMG activity (see FIG. 15, panel B). Oscillatory patterns, often clonic-like, emerged during the latter part of the periods of independent standing and then were followed by little or no EMG activity that corresponded with the loss of independence (requiring a return to manually facilitated standing). These periods of independent standing were repeated during the 60-minute standing sessions.

Thus, independent standing occurred when using stimulation having parameters selected (e.g., optimized) to facilitate standing while providing bilateral load-bearing proprioceptive input.

Locomotor Patterns with Epidural Stimulation

For stepping, epidural stimulation at 30-40 Hz and task-specific sensory cues were used to generate locomotor-like patterns. Sensory cues from manually facilitated stepping included load alternation and leg positioning with appropriate kinematics of the hips, knees, and ankles timed to the step cycle. Stepping with BWST without epidural stimulation produced little or no EMG activity (see FIG. 16, panel A). Stepping with BWST and manual facilitation in conjunction with caudal epidural stimulation resulted in an oscillatory EMG pattern in flexors and extensors (see FIG. 16, panel B). The afferent feedback determined the motor efferent pattern (see FIG. 16, panels C and D). The EMG activity in the legs was dramatically different depending on the loading and kinematic patterns when using the identical stimulation parameters. Oscillatory EMG patterns were evident only when alternating loading and flexion and extension of the lower limbs occurred (see FIG. 16, panels C and D).

Voluntary Control of Leg Movement

Voluntary (or supraspinal) control of the toe extension, ankle flexation, and leg flexion emerged only in the presence of epidural stimulation (see FIG. 17) seven months after the epidural implant that included 80 stand training sessions with epidural stimulation. Voluntary movement was observed in both limbs. However, the epidural stimulation parameters were different for each leg and technical limitations of the stimulator prevented simultaneous movements of the legs bilaterally. When the subject was instructed to flex (draw the leg upward) the toe extended, the ankle dorsi-flexed and the hip and knee flexed with the appropriate muscle activation. When instructed to dorsi-flex the ankle, the foot moved upward with tibialis anterior activation. When instructed to extend the great toe, the toe moved upward with activation of the extensor hallicus longus. For each task, the muscle activation was specific for the movement and the timing of activation was closely linked to the verbal commands (see FIGS. 17C-17E). The subject could consciously activate the appropriate muscles for the intended movement, and the timing of activation was closely linked to the verbal commands (see FIG. 17E). The ability to selectively activate different motor pools demonstrates an important feature of voluntary motor control.

Thus, locomotor-like patterns were observed when stimulation parameters were selected (e.g., optimized) to facilitate stepping. Further, seven months after implantation, the subject recovered supraspinal control of certain leg movements, but only during epidural stimulation.

Subject's Perspective

Given the uniqueness of the epidural stimulation procedures and the unusual level of commitment of the subject to the objectives of the study, the research team asked the subject his perspective on a range of highly personal topics related to changes in his health and daily living after compared to before the implant.

Interpretation of these responses should take into account that the subject received extensive rehabilitation for 170 sessions immediately before the implant. Specifically, the subject provided the following responses as to how (other than demanding so much of his time) the experience affected the specified aspect of his life:

1. sleep patterns: I am sleeping more soundly, and am able to reach a deeper level of sleep (the dream phase) almost every night. I have also noticed that I need more sleep, at least 10 hours a night and sometimes more after a hard or draining workout.

2. daily activity patterns: Besides the issue of being tired from the workouts, I have had more over all energy. I have been more active during the days than before the implant. This has improved since the first few workouts after the surgery, since at first I could not do anything and even had trouble transferring after workouts, but this has continuously gotten better every day.

3. bladder or bowel function: In terms of my bladder, I've been able to empty more often on my own, on command, without a catheter. So far I've had no infections as well. In terms of my bowel function, I'm more regular.

4. sensory function: I've been able to feel more sharp and dull sensations in places where I wasn't able to before the surgery, such as through my stomach and legs. Also I'm having better sensation with light touch throughout my midsection and legs. Refer to most recent ASIA exam where I had mostly zeros before surgery and now have mostly ones.

5. severity and frequency and timing of spasticity: My spasticity has increased only when lying down.

6. frequency and kind of medical care needed: Other than when my stitches opened shortly after surgery no medical care has been needed since surgery.

7. sexual function: Erections have been stronger and more frequent and I am able to reach full orgasm occasionally. I had never before been able to do this before the surgery.

8. diet, appetite: I feel like I get hungrier after working out, but other than that no change.

9. body weight: I've gained about 9 kilograms since surgery.

10. observable changes in muscle: My leg muscles have increased by a few inches and I am able to see definition in my quads and calfs. My upper body (biceps, triceps, shoulders etc.) have also gained inches of muscle and I have not lifted a weight since surgery. My overall core has gotten stronger and more stable.

11. posture and stability when sitting: My posture has improved. I'm more stable and have less need to hold onto things to support myself.

12. skin lesions or sensitivity to infections: I have had no infections or skin lesions.

13. other functions: I feel healthier, I have better self-esteem and confidence. My legs are heavier and more dense.

Clinical Impressions

With training and epidural stimulation, the subject had functional gains in bladder and sexual function, and temperature regulation. The subject has been able to voluntarily void with minimal residual volume, and reports normal sexual response and performance. The subject regained diaphoretic capability and ability to tolerate temperature extremes. In addition, a sense of well-being and increased self-esteem enabled more frequent social interactions. An eighteen percent gain in weight was associated with increased appetite and relative increase in lean body mass and decrease in total body fat as measured using aq DEXA scan.

Discussion

We have used an epidurally implanted electrode array to modulate the physiological state of the spinal circuitry to enable independent standing in a human with a chronic motor complete spinal cord injury. The epidural stimulation did not induce standing by directly activating motor pools, but enabled motor function by engaging populations of interneurons that integrated load-bearing related proprioceptive input to coordinate motor pool activity. This phenomenon was observed within the first week of stimulation. Although motor pool activity occurred in the presence of epidural stimulation during sitting, the functional activity needed for standing required the proprioceptive information associated with load bearing positional changes. Dynamic changes in position during standing were accompanied by motor patterns needed to maintain upright posture without changes in the epidural stimulation parameters. Intensive task specific training combined with epidural stimulation extended the duration of periods of independent standing that could be initiated by the subject.

Robust, consistent rhythmic stepping-like activity emerged during stepping only when tonic epidural stimulation and weight-bearing associated proprioception was present. When standing, the same epidural stimulation parameters elicited primarily tonic bilateral activity; however when stepping it resulted in rhythmic alternating activity. Without being limited by theory, it is believed the epidural stimulation may activate dorsal root afferent fibers and, more likely at higher intensities, dorsal columns and additional spinal structures. The continuous stimulation enabled the spinal cord to process the sensory information that is closely linked to the desired functional task by modulating the physiological state of the spinal cord. This is of great clinical importance and it allows the intervention to become feasible since the task needed can be driven and controlled by intrinsic properties of the nervous system rather than an external control system.

Our study demonstrates that the sensory input can serve as the controller of the spinal circuitry during independent standing and assisted stepping when enabled by epidural stimulation in the absence of supraspinal input in humans.

The present results show that movements of several lower limb joints can be controlled voluntarily. In subjects with a motor incomplete spinal injury, a common phenomenon is the general loss of specificity of control of selected muscles, however, the voluntary nature of these reported movements are selective. See Maegele M, Muller S, Wernig A, Edgerton V R, Harkema S J, Recruitment of spinal motor pools during voluntary movements versus stepping after human spinal cord injury, *J Neurotrauma,* 19(10):1217-1229 (October 2002). In Example 1, the activated motor pools were appropriate for the intended movement. Two possible mechanisms that might explain this result include: 1) that the epidural stimulation provided excitation of lumbosacral interneurons and motoneurons (Jankowska E., Spinal interneuronal systems: identification, multifunctional character and reconfigurations in mammals, *J Physiol,* 533 (Pt 1):31-40 (May 15, 2001)) which, combined with the weak excitatory activity of residual motor axons descending through the cervicothoracic injury, achieved a level of excitation that was sufficient to fire the motoneurons and/or 2) axonal regeneration or sprouting may have been induced via activity-dependent mechanisms occurring over a period of months. It is highly significant from a neurobiological as well as a clinical perspective that this voluntary control was manifested only in the presence of continuous tonic epidural stimulation. This demonstrates that by elevating the level of spinal interneuronal excitability to some critical, but sub-threshold level, voluntary movements can be regained. Dimitrijevic M R, Gerasimenko Y, Pinter M M, Evidence for a spinal central pattern generator in humans, *Ann NY Acad Sci,* 16; 860:360-376 (November 1998). These same mechanisms may also explain the improved autonomic function in bladder, sexual, vasomotor, and thermoregulatory activity that has been of benefit to the subject. The areas of lumbosacral spinal cord stimulated included at least parts of the neural circuits that regulate these autonomic functions and may have also resulted in activity-dependent changes. In other words, given that the broad areas of the lumbosacral spinal cord stimulated include at least parts of the neural circuits that regulate these autonomic functions, these changes might have been expected if the neural networks controlling these autonomic functions are activity-dependent.

These data demonstrate that humans have conserved spinal locomotor circuitry as found in other mammals that include: 1) transition from a low level activity state to one that can generate active standing in the presence of tonic epidural stimulation; 2) gate tonic electrically evoked responses according to the task specific sensory input, resulting in specific patterns of coordination within and between the motor pools; 3) use appropriate task specific sensory input to control the level and timing of neural excitation sufficient to generate independent standing and facilitate stepping; and 4) to mediate voluntarily initiated movement of the lower limbs in the presence of epidural stimulation. A higher level of improvement in motor function may be achieved with the addition of pharmacological agents not only in spinal cord injury but also with other neuromotor disorders. See Fuentes R, Petersson P, Siesser W B, Caron M G, Nicolelis M A, Spinal cord stimulation restores locomotion in animal models of Parkinson's disease, *Science,* 323(5921):1578-1582 (Mar. 20, 2009).

In Example 1, epidural stimulation of the human spinal cord circuitry combined with task specific proprioceptive input resulted in novel postural and locomotor patterns. After seven months of stimulation and stand training, supraspinally mediated movements of the legs were manifested only in the presence of epidural stimulation. Task specific training with epidural stimulation may have reactivated previously silent spared neural circuits or promoted plasticity. Thus, such interventions may provide a viable clinical approach for functional recovery after severe paralysis.

The above example supports the following. First, it is possible to stimulate the lumbosacral spinal cord with a modest, but sufficient level of intensity to enable the sensory input from the lower limbs to serve as a source of control of standing and to some degree of stepping. Second, the ability to stand for greater durations increases with daily stand training. Third, after months of stand training in the presence of epidural stimulation, there was sufficient supraspinal and spinal reorganization to enable conscious control of movements of the lower limbs. Fourth, extensive reorganization of supraspinal and spinal motor systems can occur in response to activity-dependent interventions in an individual with complete paralysis for more than 3 years after a lower cervical-upper thoracic spinal cord injury. None of these observations in a human subject with this severity of injury have been made previously.

Some additional publications discussing related technologies include the following:

1. Gerasimenko Y, Roy R R, Edgerton V R., Epidural stimulation: comparison of the spinal circuits that generate and control locomotion in rats, cats and humans, *Exp Neurol*, 209(2):417-425 (February 2008);
2. Grillner S, Wallen Peter, Central pattern generators for locomotion, with special reference to vertebrates, *Ann Rev Neurosci*, 8:233-261 (1985);
3. Grillner S., The motor infrastructure: from ion channels to neuronal networks, *Nat Rev Neurosci*, 4(7):573-586 (July 2003);
4. Grillner S, Zangger P., On the central generation of locomotion in the low spinal cat, *Exp Brain Res;* 34:241-261 (1979);
5. de Leon R D, Hodgson J A, Roy R R, Edgerton V R., Full weight-bearing hindlimb standing following stand training in the adult spinal cat, *J Neurophysiol*, 80:83-91 (1998);
6. Harkema S, Schmidt-Read M, Lorenz D, Edgerton V R, Behrman A., Functional recovery in individuals with chronic incomplete spinal cord injury with intensive activity-based rehabilitation, *Arch Phys Med Rehab*, InPress;
7. Minassian K, Persy I, Rattay F, et al., Human lumbar cord circuitries can be activated by extrinsic tonic input to generate locomotor-like activity, *Hum Mov Sci,* 26:275-95 (2007);
8. Jilge B, Minassian K, Rattay F, et al., Initiating extension of the lower limbs in subjects with complete spinal cord injury by epidural lumbar cord stimulation, *Exp Brain Res*, 154(3):308-26 (2004); and
9. Fuentes R, Petersson P, Siesser W B, Caron M G, Nicolelis M A., Spinal cord stimulation restores locomotion in animal models of Parkinson's disease, *Science*, 323(5921):1578-1582 (Mar. 20, 2009).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

We claim:
1. A method comprising:
applying an electrical stimulation to a portion of a spinal cord of a neurologically paralyzed patient in conjunction with physical training of a paralyzed portion of the neurologically paralyzed patient, and
administering one or more neuropharmaceutical agents to the neurologically paralyzed patient,
wherein the electrical stimulation is below an amount that fully activates a spinal circuit such that the spinal circuit is at least partially activatable by the addition of supraspinal signals.

2. The method of claim 1, wherein the neurologically paralyzed patient has a motor complete paralysis or a motor incomplete paralysis.

3. The method of claim 1, wherein the electrical stimulation does not directly activate muscle cells in the paralyzed portion of the patient's body.

4. The method of claim 1, wherein the physical training provides induced neurological signals, and the induced neurological signals comprise at least one of postural proprioceptive signals, locomotor proprioceptive signals, and the supraspinal signals.

5. The method of claim 1, wherein the neurologically paralyzed patient has a spinal cord injury classified as motor complete or motor incomplete.

6. The method of claim 1, wherein the neurologically paralyzed patient had an ischemic brain injury, a traumatic brain injury, or a neurodegenerative brain injury.

7. The method of claim 6, wherein the neurodegenerative brain injury is associated with at least one of Parkinson's disease, Huntington's disease, Alzheimer's, ischemia, stroke, amyotrophic lateral sclerosis (ALS), primary lateral sclerosis (PLS), and cerebral palsy.

8. The method of claim 1, wherein the applying the electrical stimulation is by an electrode array that is implanted epidurally at the spinal cord of the patient.

9. The method of claim 1, wherein the physical training comprises at least one of standing, stepping, reaching, moving one or both legs, moving one or both feet, grasping, and stabilizing sitting posture.

10. The method of claim 1, wherein the applying the electrical stimulation:
    enables voluntary movement of muscles involved in at least one of standing, stepping, reaching, grasping, voluntarily changing positions of one or both legs, voiding the patient's bladder, voiding the patient's bowel, postural activity, and locomotor activity,
    enables or improves autonomic control of at least one of cardiovascular function, body temperature, and metabolic processes, or
    facilitates recovery of at least one of an autonomic function, sexual function, vasomotor function, and cognitive function.

11. The method of claim 1, wherein the neuropharmaceutical agent is a serotonergic drug, a dopaminergic drug, a noradrenergic drug, a GABAergic drug, a glycinergic drug, or a combination thereof.

12. A method of enabling one or more bodily functions in a neurologically paralyzed patient, the method comprising:
    stimulating the spinal cord of the neurologically paralyzed patient using an electrode array while subjecting the neurologically paralyzed patient to physical training, and
    administering one or more neuropharmaceutical agents to the neurologically paralyzed patient,
    wherein at least one of the stimulating or physical training activates at least one spinal circuit by at least one of supraspinal information and proprioceptive information derived from the region of the neurologically paralyzed patient where the one or more bodily functions occur.

13. The method of claim 12, wherein the one or more bodily functions is selected from postural and/or locomotor activity, voluntary movement of leg position when not bearing weight, voluntary voiding of the bladder and/or bowel, return of sexual function, autonomic control of cardiovascular function, body temperature control, normalized metabolic processes, or a combination thereof.

14. The method of claim 12, wherein the region where the region of the neurologically paralyzed patient where the one or more bodily functions occur are lower limbs or upper limbs.

15. The method of claim 12, wherein the physical training comprises at least one of standing, stepping, sitting down, laying down, reaching, grasping, stabilizing sitting posture, and stabilizing standing posture.

16. The method of claim 12, wherein the electrode array comprises one or more electrodes stimulated in a monopolar configuration or bipolar configuration.

17. The method of claim 12, wherein the stimulating comprises at least one of tonic stimulation and intermittent stimulation.

18. The method of claim 12, wherein the physical training comprises inducing a positional or physical change in a region of the neurologically paralyzed patient.

19. The method according to claim 18, wherein the positional or physical change in the neurologically paralyzed patient comprises at least one of standing, stepping, reaching, and grasping.

20. The method of claim 12, wherein the one or more neuropharmaceutical agents comprises a serotonergic drug, a dopaminergic drug, a noradrenergic drug, a GABAergic drug, a glycinergic drug, or a combination thereof.

* * * * *